US008288370B2

(12) United States Patent  (10) Patent No.: US 8,288,370 B2
Bergman et al. (45) Date of Patent: Oct. 16, 2012

(54) SUBSTITUTED AZETIDINE COMPOUNDS OF FORMULA (I) USEFUL IN THE TREATMENT OF FUNCTIONAL GASTROINTESTINAL DISORDERS, IBS, AND FUNCTIONAL DYSPEPSIA

(75) Inventors: Rolf Bergman, Molndal (SE); Sara Holmqvist, Molndal (SE); Sverker Von Unge, Molndal (SE)

(73) Assignee: Albireo AB, Gothenburg (SE)

( * ) Notice: Subject to any disclaimer, the term of this patent is extended or adjusted under 35 U.S.C. 154(b) by 211 days.

(21) Appl. No.: 11/992,701

(22) PCT Filed: Sep. 27, 2006

(86) PCT No.: PCT/SE2006/001092
§ 371 (c)(1),
(2), (4) Date: Aug. 25, 2010

(87) PCT Pub. No.: WO2007/037743
PCT Pub. Date: Apr. 5, 2007

(65) Prior Publication Data
US 2010/0311713 A1    Dec. 9, 2010

(30) Foreign Application Priority Data

Sep. 29, 2005   (SE) ..................................... 0502150

(51) Int. Cl.
A61K 31/00 (2006.01)
(52) U.S. Cl. ...................... 514/210.2; 544/349; 544/350; 544/386; 548/950; 549/429
(58) Field of Classification Search ................ 514/210.2; 544/349, 350, 386; 548/950; 549/429
See application file for complete search history.

(56) References Cited

U.S. PATENT DOCUMENTS

| | | | |
|---|---|---|---|
| 6,013,652 A | 1/2000 | Maccoss et al. | |
| 6,906,058 B2 | 6/2005 | Starke et al. | |
| 7,125,864 B2 | 10/2006 | Starke et al. | |
| 7,132,416 B2 | 11/2006 | Starke et al. | |
| 7,192,945 B2 | 3/2007 | Starke et al. | |
| 7,192,946 B2 | 3/2007 | Starke et al. | |
| 7,192,947 B2 | 3/2007 | Starke et al. | |
| 7,226,943 B2 | 6/2007 | Starke et al. | |
| 7,238,684 B2 | 7/2007 | Starke et al. | |
| 7,402,581 B2 | 7/2008 | Johansson et al. | |
| 7,514,421 B2 | 4/2009 | Abrahamsson et al. | |
| 8,067,584 B2 | 11/2011 | Starke et al. | |
| 8,106,208 B2 | 1/2012 | Johansson et al. | |
| 2006/0083790 A1 | 4/2006 | Anderberg et al. | |
| 2007/0248995 A1 | 10/2007 | Drmota et al. | |
| 2007/0270399 A1 | 11/2007 | Fredenwall et al. | |
| 2007/0270400 A1* | 11/2007 | Johansson .................. | 514/210.2 |
| 2008/0146538 A1 | 6/2008 | Antonsson | |
| 2010/0069346 A1 | 3/2010 | Holmqvist et al. | |

FOREIGN PATENT DOCUMENTS

| | | |
|---|---|---|
| EP | 0625509 A1 | 11/1994 |
| EP | 0630887 A1 | 12/1994 |
| EP | 0790248 | 8/1997 |
| EP | 0791592 | 8/1997 |
| EP | 0962457 | 8/1999 |
| WO | WO 95/05377 | 2/1995 |
| WO | WO 95/12577 | 5/1995 |
| WO | WO 95/15961 | 6/1995 |
| WO | WO96/05193 | 2/1996 |
| WO | WO-96/10568 A1 | 4/1996 |
| WO | WO96/24582 | 8/1996 |
| WO | WO97/25322 | 7/1997 |
| WO | WO-97/27185 A1 | 7/1997 |
| WO | WO-00/02859 A1 | 1/2000 |
| WO | WO-00/20003 A1 | 4/2000 |
| WO | WO0020389 | 4/2000 |
| WO | WO/0025766 | 5/2000 |
| WO | WO-00/34243 A1 | 6/2000 |
| WO | WO02/051807 | 7/2002 |
| WO | WO03/037889 | 5/2003 |
| WO | WO 03/066635 | 8/2003 |
| WO | WO-2004/041279 A1 | 5/2004 |
| WO | WO-2004/110344 A2 | 12/2004 |

(Continued)

OTHER PUBLICATIONS

Lima, et al. Current Med. Chem., 12, 2005, 23-49.*
PCT Application PCT/SE2006/001092, International Search Report mailed Jan. 22, 2007, 11 pgs.
Mackenzie, A. R., "4-Amino-2-(aryl)-butylbenzamides and Their Conformationally Constrained Analogues. Potent Antagonists of the Human Neurokinin-2 (NK$_2$) Receptor", *Bioorganic & Medicinal Chemistry Letters*, 13 (2003), 2211-2215.
Arvidsson et al. "Assessment of visceral pain-related pseudo-affective responses to colorectal distension in mice by intracolonic manometric recordings." *J. Pain.*, 2006, 7:108-118.

(Continued)

*Primary Examiner* — Douglas M Willis
(74) *Attorney, Agent, or Firm* — Fish & Richardson P.C.

(57) ABSTRACT

The present invention relates to new substituted azetidine compounds of formula (I):

(I)

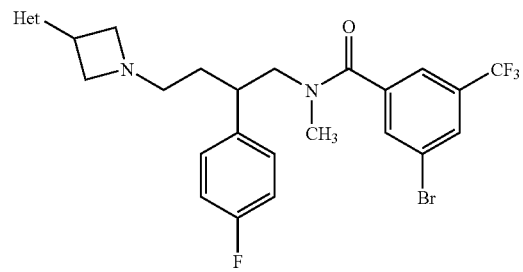

or pharmaceutically acceptable salts thereof, as further described herein, to pharmaceutical compositions containing them, and the use of the compounds in the treatment of functional gastrointestinal disorders, IBS, and functional dyspepsia. The compounds are neurokinin (NK) antagonists. The present invention further relates to processes for the preparation of the compounds.

20 Claims, No Drawings

FOREIGN PATENT DOCUMENTS

| WO | WO2006/137791 | | 12/2006 |
|---|---|---|---|
| WO | WO 2006/137791 | * | 12/2006 |

OTHER PUBLICATIONS

Bapiro et al. "Application of Higher Throughput Screening (HTS) Inhibition Assays to Evaluate the Interaction of Antiparasitic Drugs with Cytochrome P45os." *Drug Metab. Dispos.*, 2001, 29:30-35.

Cheng and Prusoff. "Relationship between the inhibition constant (K1) and the concentration of inhibitor which causes 50 per cent inhibition (150) of an enzymatic reaction." *Biochem Pharmacol.*, 1973, 22:3099-3108.

Jung and Choi. "New Synthesis of 2-Azetines and 1-Azabutadienes and the Use of the Latter in Diels-Alder Reactions; Total Synthesis of (±) δ- Coniceine." *J.Org. Chem.*, 1991, 56(24):6729-6730.

Kiss et al. "High throughput ion-channel pharmacology; planar-array-based voltage clamp." *Assay Drug Dev Thechnol.*, 2003, 1:127-135.

Kumar et al. "Cyclic amine sulfonamides as linkers in the design and synthesis of novel human beta (3) adrenergic receptor agonists." *Bioorg. Med. Chem. Lett.*, 2003, 13:2191-2194.

Okano et al. "Effects of TAK- 637, a Novel Neurokinin-1 Receptor Antagonist, on Colonic Function in Vivo." *The Journal of Pharmacology and Experimental Therapeutics*, 2001, Colonic 298:559-564.

Scapecchi et al. "Structure—activity relationship studies on unifiram (DM232) and sunifiram (DM235), two novel and potent cognition enhancing drugs." *Bioorg. Med. Chem.*, 2004, 12:71-85.

Tammpere at al. "Evaluation of pseudo-affective responses to noxious colorectal distension in rats by manometric recordings." *PAIN.*, 2005, 116:220-226.

Vandenberg et al, "HERG K+ channels: friend and foe." *Trends Pharmacol Sci*. 2001, 22:240-246.

* cited by examiner

SUBSTITUTED AZETIDINE COMPOUNDS OF FORMULA (I) USEFUL IN THE TREATMENT OF FUNCTIONAL GASTROINTESTINAL DISORDERS, IBS, AND FUNCTIONAL DYSPEPSIA

RELATED APPLICATIONS

This application is a nationalization under 35 U.S.C. 371 of PCT/SE2006/001092, filed Sep. 27, 2006 and published as WO 2007/037743 A1, on Apr. 5, 2007, which claimed priority under 35 U.S.C. 119 to Sweden Patent Application Serial No. 0502150-6, filed Sep. 29, 2005; which applications and publication are incorporated herein by reference and made a part hereof.

FIELD OF THE INVENTION

The present invention relates to new compounds of formula I, to pharmaceutical compositions containing said compounds, and to the use of said compounds in therapy. The present invention further relates to processes for the preparation of compounds of formula I and to new intermediates thereof.

BACKGROUND OF THE INVENTION

The neurokinins, also known as the tachykinins, comprise a class of peptide neurotransmitters which are found in the peripheral and central nervous systems. The three principal tachykinins are Substance P (SP), Neurokinin A (NKA) and Neurokinin B (NKB). At least three receptor types are known for the three principal tachykinins. Based upon their relative selectivities favouring the agonists SP, NKA and NKB, the receptors are classified as neurokinin 1 ($NK_1$), neurokinin 2 ($NK_2$) and neurokinin 3 ($NK_3$) receptors, respectively.

There is a need for an orally active NK receptor antagonist for the treatment of e.g. respiratory, cardiovascular, neuro, pain, oncology, inflammatory and/or gastrointestinal disorders. In order to increase the therapeutic index of such therapy it is desirable to obtain such a compound possessing no or minimal toxicity as well as being selective to said NK receptors. Furthermore, it is considered necessary that said medicament has favourable pharmacokinetic and metabolic properties thus providing an improved therapeutic and safety profile such as lower liver enzyme inhibiting properties.

It is well known that severe problems such as toxicity may occur if plasma levels of one medication are altered by the co-administration of another drug. This phenomenon—which is named drug-drug interactions—could happen if there is a change in the metabolism of one drug caused by the co-administration of another substance possessing liver enzyme inhibiting properties. CYP (cytochrome P450) 3A4 is the most important enzyme in the human liver as a majority of oxidised drugs have been biotransformed by this enzyme. Accordingly, it is undesirable to employ a medication having a significant degree of such liver enzyme inhibiting properties. It has been found that many NK receptor antagonists known in the art inhibit the CYP3A4 enzyme to a certain level and consequently there is a possible risk if high doses of those compounds are being used in therapy. Thus, there is a need for a novel NK receptor antagonist with improved pharmacokinetic properties. The present invention provides compounds with CYP3A4 enzyme inhibiting properties at a low level, as comparatively high $IC_{50}$ values are obtained in a CYP3A4 inhibiting assay. Said method for determining CYP3A4 inhibition is described in Bapiro et al; Drug Metab. Dispos. 29, 30-35 (2001).

It is well known that certain compounds may cause undesirable effects on cardiac repolarisation in man, observed as a prolongation of the QT interval on electrocardiograms (ECG). In extreme circumstances, this drug-induced prolongation of the QT interval can lead to a type of cardiac arrhythmia called Torsades de Pointes (TdP; Vandenberg et al. hERG $K^+$ channels: friend and foe. Trends Pharmacol Sci 2001; 22: 240-246), leading ultimately to ventricular fibrillation and sudden death. The primary event in this syndrome is inhibition of the rapid component of the delayed rectifying potassium current (IKr) by these compounds. The compounds bind to the aperture-forming alpha sub-units of the channel protein carrying this current. The aperture-forming alpha sub-units are encoded by the human ether-a-go-go-related gene (hERG). Since IKr plays a key role in repolarisation of the cardiac action potential, its inhibition slows repolarisation and this is manifested as a prolongation of the QT interval. Whilst QT interval prolongation is not a safety concern per se, it carries a risk of cardiovascular adverse effects and in a small percentage of people it can lead to TdP and degeneration into ventricular fibrillation.

In particular, it is desirable that the NK receptor antagonist has a suitable balance of pharmacodynamic and pharmacokinetic properties to make it therapeutically useful. In addition to having sufficient and selective potency, the NK receptor antagonist needs to be balanced with regard to relevant pharmacokinetic properties. Thus, it is necessary that the NK antagonist has: a) sufficiently high affinities at the different NK receptors, b) pharmacokinetic properties (absorption, distribution and elimination properties) that makes it possible for the drug to act at the targeted NK receptors in the periphery as well as in the CNS. For instance, the NK receptor antagonist needs to have sufficiently high metabolic stability, c) sufficiently low affinities to different ion channels, such as the hERG-encoded potassium channel in order to obtain a tolerable safety profile and d) liver enzyme (such as CYP3A4) inhibiting properties at a low level to prevent drug-drug interactions. Furthermore, in order to enhance the efficacy of the NK receptor antagonist, it is beneficial to have an NK antagonist with a long-lasting competitive mode of action at the receptor.

EP 0625509, EP 0630887, WO 95/05377, WO 95/12577, WO 95/15961, WO 96/24582, WO 00/02859, WO 00/20003, WO 00/20389, WO 00/25766, WO 00/34243, WO 02/51807 and WO 03/037889 disclose piperidinylbutylamide derivatives, which are tachykinin antagonists.

"4-Amino-2-(aryl)-butylbenzamides and Their Conformationally Constrained Analogues. Potent Antagonists of the Human Neurokinin-2 ($NK_2$) Receptor", Roderick MacKenzie, A., et al, *Bioorganic & Medicinal Chemistry Letters* (2003), 13, 2211-2215, discloses the compound N-[2-(3,4-dichlorophenyl)-4-(3-morpholin-4-ylazetidin-1-yl)butyl]-N-methylbenzamide which was found to possess functional $NK_2$ receptor antagonistic properties.

WO 96/05193, WO 97/27185 and EP 0962457 disclose azetidinylalkyllactam derivatives with tachykinin antagonist activity.

EP 0790248 discloses azetidinylalkylazapiperidones and azetidinylalkyloxapiperidones, which are stated to be tachykinin antagonists.

WO 99/01451 and WO 97/25322 disclose azetidinylalkylpiperidine derivatives claimed to be tachykinin antagonists.

EP 0791592 discloses azetidinylalkylglutarimides with tachykinin antagonistic properties.

WO2004/110344 A2 discloses dual NK1,2 antagonists and the use thereof.

An object of the present invention was to provide novel neurokinin antagonists useful in therapy. A further object was to provide novel compounds having well-balanced to pharmacokinetic and pharmacodynamic properties.

Outline of the Invention

The present invention provides a compound of the general formula (I)

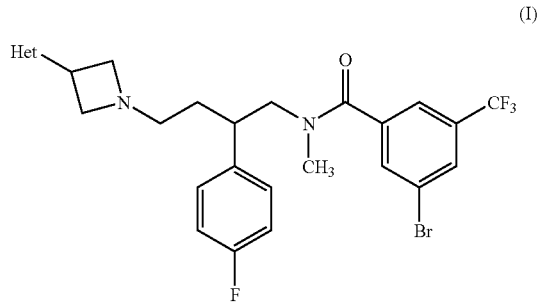

wherein
Het is

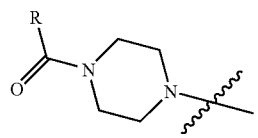

wherein
R is $C_1$-$C_4$ alkyl; cyclopropyl; $C_1$-$C_4$ methoxyalkyl; $C_1$-$C_4$ ethoxyalkyl; $C_1$-$C_4$ hydroxyalkyl; tetrahydrofuran-2-yl; tetrahydrofuran-3-yl; tetrahydropyran-2-yl; tetrahydropyran-3-yl; or tetrahydropyran-4-yl;
or Het is

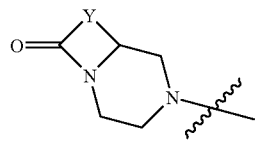

wherein
Y is $C_1$-$C_3$ alkyl; —$CH_2$—O—$CH_2$—; or —$CH_2$—$CH_2$—O—;
as well as pharmaceutically and pharmacologically acceptable salts thereof, and enantiomers of the compound of formula I and salts thereof.

In one embodiment of the present invention, R is $C_1$-$C_4$ alkyl; $C_1$-$C_4$ methoxyalkyl; $C_1$-$C_4$ ethoxyalkyl; $C_1$-$C_4$ hydroxyalkyl; tetrahydrofuran-2-yl; tetrahydrofuran-3-yl; tetrahydropyran-2-yl; tetrahydropyran-3-yl; or tetrahydropyran-4-yl. In a further embodiment of the present invention, R is $C_1$-$C_3$ alkyl. In yet another embodiment, R is $C_3$ alkyl. In another embodiment, R is cyclopropyl. In another embodiment of the present invention, R is $C_1$-$C_2$ methoxyalkyl. In another embodiment of the present invention, R is $C_1$-$C_2$ ethoxyalkyl.

In one embodiment of the present invention, Y is $C_2$-$C_3$ alkyl. In another embodiment, Y is —$CH_2$—O—$CH_2$—.

In a further embodiment of the present invention, the compound of formula I is the S-enantiomer.

The present invention relates to compounds of formula I as defined above as well as to salts thereof. Salts for use in pharmaceutical compositions will be pharmaceutically acceptable salts, but other salts may be useful in the production of the compounds of formula I.

The compounds of the present invention are capable of forming salts with various inorganic and organic acids and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, palmoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate.

Pharmaceutically acceptable salts may be prepared from the corresponding acid in conventional manner. Non-pharmaceutically-acceptable salts may be useful as intermediates and as such are another aspect of the present invention.

Acid addition salts may also be in the form of polymeric salts such as polymeric sulfonates.

The salts may be formed by conventional means, such as by reacting the free base form of the product with one or more equivalents of the appropriate acid in a solvent or medium in which the salt is poorly soluble, or in a solvent such as water, which is removed in vacuo or by freeze drying or by exchanging the anions of an existing salt for another anion on a suitable ion-exchange resin.

Compounds of formula I have one or more chiral centres, and it is to be understood that the invention encompasses all optical isomers, enantiomers and diastereomers. The compounds according to formula (I) can be in the form of the single stereoisomers, i.e. the single enantiomer (the R-enantiomer or the S-enantiomer) and/or diastereomer. The compounds according to formula (I) can also be in the form of a racemic mixture, i.e. an equimolar mixture of enantiomers.

The compounds can exist as a mixture of conformational isomers. The compounds of this invention comprise both mixtures of, and individual, conformational isomers.

As used herein, the term "$C_1$-$C_4$ alkyl" includes straight as well as branched chain $C_{1-4}$ alkyl groups, for example methyl, ethyl, n-propyl, i-propyl, n-butyl, i-butyl, s-butyl or t-butyl.

As used herein, "$C_1$-$C_4$ hydroxyalkyl" is a hydroxyalkyl group comprising 1-4 carbon atoms and a hydroxyl group.

As used herein, "$C_1$-$C_4$ methoxyalkyl" is a methoxyalkyl group comprising 1-4 carbon atoms in the alkyl chain and a methoxy group.

As used herein, "$C_1$-$C_4$ ethoxyalkyl" is an ethoxyalkyl group comprising 1-4 carbon atoms in the alkyl chain and an ethoxy group.

Pharmaceutical Formulations

According to one aspect of the present invention there is provided a pharmaceutical formulation comprising a compound of formula I, as a single enantiomer, a racemate or a mixture thereof as a free base or pharmaceutically acceptable salts thereof, for use in prevention and/or treatment of respiratory, cardiovascular, neuro, pain, oncology, inflammatory and/or gastrointestinal disorders.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, pellets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans in a daily dose of a compound of formula I of from 0.01 to 25 mg/kg body weight. Alternatively, a daily dose of the compound of formula I from 0.1 to 5 mg/kg body weight is administered. This daily dose may be given in divided doses as necessary, the precise amount of the compound administered and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of from 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Medical and Pharmaceutical Use

The present invention provides a method of treating or preventing a disease condition wherein antagonism of tachykinins acting at the NK receptors is beneficial which comprises administering to a subject an effective amount of a compound of the formula (I) or a pharmaceutically-acceptable salt thereof. The present invention also provides the use of a compound of the formula (I) or a pharmaceutically acceptable salt thereof in the preparation of a medicament for use in a disease condition wherein antagonism of tachykinins acting at the NK receptors is beneficial.

The compounds of formula (I) or pharmaceutically acceptable salts or solvates thereof may be used in the manufacture of a medicament for use in the prevention or treatment of respiratory, cardiovascular, neuro, pain, oncology and/or gastrointestinal disorders.

Examples of such disorders are asthma, allergic rhinitis, pulmonary diseases, cough, cold, inflammation, chronic obstructive pulmonary disease, airway reactivity, urticaria, hypertension, rheumatoid arthritis, edema, angiogenesis, pain, migraine, tension headache, psychoses, depression, anxiety, Alzheimer's disease, schizophrenia, Huntington's disease, bladder hypermotility, urinary incontinence, eating disorder, manic depression, substance dependence, movement disorder, cognitive disorder, obesity, stress disorders, micturition disorders, mania, hypomania and aggression, bipolar disorder, cancer, carcinoma, fibromyalgia, non cardiac chest pain, gastrointestinal hypermotility, gastric asthma, Crohn's disease, gastric emptying disorders, ulcerative colitis, irritable bowel syndrome (IBS), inflammatory bowel disease (IBD), emesis, gastric asthma, gastric motility disorders, gastro-esophageal reflux disease (GERD) or functional dyspepsia.

Pharmacology

Transfection and Culturing of Cells Used in FLIPR and Binding Assays

Chinese Hamster Ovary (CHO) K1 cells (obtained from ATCC) were stably transfected with the human $NK_2$ receptor ($hNK_2R$ cDNA in pRc/CMV, Invitrogen) or the human $NK_3$ receptor ($hNK_3R$ in pcDNA 3.1/Hygro (+)/IRES/CD8, Invitrogen vector modified at AstraZeneca EST-Bio UK, Alderley Park). The cells were transfected with the cationic lipid reagent LIPOFECTAMINE™ (Invitrogen) and selection was performed with Geneticin (G418, Invitrogen) at 1 mg/ml for the $hNK_2R$ transfected cells and with Hygromycin (Invitrogen) at 500 µg/ml for the $hNK_3R$ transfected cells. Single cell clones were collected by aid of Fluorescence Activated Cell Sorter (FACS), tested for functionality in a FLIPR assay (see below), expanded in culture and cryopreserved for future use. CHO cells stably transfected with human $NK_1$ receptors originates from AstraZeneca R&D, Wilmington USA. Human $NK_1$ receptor cDNA (obtained from RNA-PCR from lung tissue) was subcloned into pRcCMV (Invitrogen). Transfection was performed by Calcium Phosphate and selection with 1 mg/ml G418.

The CHO cells stably transfected with $hNK_1R$, $hNK_2R$ and $hNK_3R$ were cultured in a humidified incubator under 5% $CO_2$, in Nut Mix F12 (HAM) with Glutamax I, 10% Foetal Bovine Serum (FBS), 1% Penicillin/Streptomycin (PEST) supplemented with 200 µg/ml Geneticin for the $hNK_1R$ and $hNK_2R$ expressing cells and 500 µg/ml Hygromycin for the $hNK_3R$ expressing cells. The cells were grown in T175 flasks and routinely passaged when 70-80% confluent for up to 20-25 passages.

Assessing the Activity of Selected Test Compounds to Inhibit Human $NK_1/NK_2/NK_3$ Receptor Activation (FLIPR Assay)

The activity of a compound of the invention to inhibit $NK_1/NK_2/NK_3$ receptor activation measured as $NK_1/NK_2/NK_3$ receptor mediated increase in intracellular $Ca^{2+}$ was assessed by the following procedure:

CHO cells stably transfected with human $NK_1$, $NK_2$ or $NK_3$ receptors were plated in black walled/clear bottomed 96-well plates (Costar 3904) at $3.5 \times 10^4$ cells per well and grown for approximately 24 h in normal growth media in a 37° C. $CO_2$-incubator.

Before the FLIPR assay the cells of each 96-well plate were loaded with the $Ca^{2+}$ sensitive dye Fluo-3 (TEFLABS 0116) at 4 µM in a loading media consisting of Nut Mix F12 (HAM) with Glutamax I, 22 mM HEPES, 2.5 mM Probenicid (Sigma P-8761) and 0.04% Pluronic F-127 (Sigma P-2443) for 1 h kept dark in a 37° C. $CO_2$-incubator. The cells were then washed three times in assay buffer (Hanks balanced salt solution (HBSS) containing 20 mM HEPES, 2.5 mM Probenicid and 0.1% BSA) using a multi-channel pipette leaving them in 150 µl at the end of the last wash. Serial dilutions of a test compound in assay buffer (final DMSO concentration kept below 1%) were automatically pipetted by FLIPR (Fluorometric Imaging Plate Reader) into each test well and the fluorescence intensity was recorded (excitation 488 nm and emission 530 nm) by the FLIPR CCD camera for a 2 min pre-incubation period. 541 of the Substance P($NK_1$ specific), NKA ($NK_2$ specific), or Pro-7-NKB ($NK_3$ specific) agonist solution (final concentration equivalent to an approximate $EC_{60}$ concentration) was then added by FLIPR into each well already containing 200 μl assay buffer (containing the test compound or vehicle) and the fluorescence was continuously monitored for another 2 min. The response was measured as the peak relative fluorescence after agonist addition and $IC_{50}$s were calculated from ten-point concentration-response curves for each compound. The $IC_{50}$s were then converted to $pK_B$ values with the following formula:

$$K_B = IC_{50}/1 + (EC_{60} \text{ conc. of agonist used in assay}/EC_{50} \text{ agonist})$$

$$pK_B = -\log K_B$$

Determining the Dissociation Constant (Ki) of Compounds for Human $NK_1/NK_2/NK_3$ Receptors (Binding Assay)

Membranes were prepared from CHO cells stably transfected with human $NK_1$, $NK_2$ or $NK_3$ receptors according to the following method.

Cells were detached with Accutase® solution, harvested in PBS containing 5% FBS by centrifugation, washed twice in PBS and resuspended to a concentration of $1 \times 10^8$ cells/ml in Tris-HCl 50 mM, KCl 300 mM, EDTA-$N_2$ 10 mM pH 7.4 (4° C.). Cell suspensions were homogenized with an UltraTurrax 30 s 12.000 rpm. The homogenates were centrifuged at 38.000×g (4° C.) and the pellet resuspended in Tris-HCl 50 mM pH 7.4. The homogenization was repeated once and the homogenates were incubated on ice for 45 min. The homogenates were again centrifuged as described above and resuspended in Tris-HCl 50 mM pH 7.4. This centrifugation step was repeated 3 times in total. After the last centrifugation step the pellet was resuspended in Tris-HCl 50 mM and homogenized with Dual Potter, 10 strokes to a homogenous solution, an aliquot was removed for protein determination. Membranes were aliquoted and frozen at −80° C. until use.

The radioligand binding assay is performed at room temperature in 96-well microtiter plates (No-binding Surface Plates, Corning 3600) with a final assay volume of 200 μl/well in incubation buffer (50 mM Tris buffer (pH 7.4 RT) containing 0.1% BSA, 40 mg/L Bacitracin, complete EDTA-free protease inhibitor cocktail tablets 20 pills/L (Roche) and 3 mM $MnCl_2$). Competition binding curves were done by adding increasing amounts of the test compound. Test compounds were dissolved and serially diluted in DMSO, final DMSO concentration 1.5% in the assay. 50 μl Non labelled ZD 6021 (a non selective NK-antagonist, 10 μM final conc) was added for measurement of non-specific binding. For total binding, 50 μl of 1.5% DMSO (final conc) in incubation buffer was used. [$^3$H-Sar,Met($O_2$)-Substance P] (4 nM final conc) was used in binding experiments on $hNK_1r$. [$^3$H-SR48968] (3 nM final conc.) for $hNK_2r$ and [$^3$H-SR142801] (3 nM final conc) for binding experiments on $hNK_3r$. 50 μl radioligand, 3 μl test compound diluted in DMSO and 47 μl incubation buffer were mixed with 5-10 μg cell membranes in 100 μl incubation buffer and incubated for 30 min at room temperature on a microplate shaker.

The membranes were then collected by rapid filtration on Filtermat B(Wallac), presoaked in 0.1% BSA and 0.3% Polyethyleneimine (Sigma P-3143), using a Micro 96 Harvester (Skatron Instruments, Norway). Filters were washed by the harvester with ice-cold wash buffer (50 mM Tris-HCl, pH 7.4 at 4° C., containing 3 mM $MnCl_2$) and dried at 50° C. for 30-60 min. Meltilex scintillator sheets were melted on to filters using a Microsealer (Wallac, Finland) and the filters were counted in a β-Liquid Scintillation Counter (1450 Microbeta, Wallac, Finland).

The $K_i$ value for the unlabeled ligand was calculated using the Cheng-Prusoff equation (Biochem. Pharmacol. 22:3099-3108, 1973): where L is the concentration of the radioactive ligand used and $K_d$ is the affinity of the radioactive ligand for the receptor, determined by saturation binding.

Data was fitted to a four-parameter equation using Excel Fit.

$$K_i = IC_{50}/(1 + (L/K_d))$$

Results

In general, the compounds of the invention, which were tested, demonstrated statistically significant antagonistic activity at the $NK_1$ receptor within the range of 8-9 for the $pK_B$. For the $NK_2$ receptor the range for the $pK_B$ was 7-9. In general, the antagonistic activity at the $NK_3$ receptor was 7-9 for the $pK_B$.

In general, the compounds of the invention, which were tested, demonstrated statistically significant CYP3A4 inhibition at a low level. The $IC_{50}$ values tested according to Bapiro et al; Drug Metab. Dispos. 29, 30-35 (2001) were generally greater than 15 μM.

Activity Against hERG

The activity of compounds according to formula I against the hERG-encoded potassium channel can be determined according to Kiss L, et al. Assay Drug Dev Technol. 1 (2003), 127-35: "High throughput ion-channel pharmacology: planar-array-based voltage clamp".

In general, the compounds of the invention, which were tested, demonstrated statistically significant hERG activity at a low level. The $IC_{50}$ values tested as described above were generally greater than 10 μM.

Metabolic Stability

The metabolic stability of compounds according to formula I can be determined as described below:

The rate of biotransformation can be measured as either metabolite(s) formation or the rate of disappearance of the parent compound. The experimental design involves incubation of low concentrations of substrate (usually 1.0 μM) with liver microsomes (usually 0.5 mg/ml) and taking out aliquotes at varying time points (usually 0, 5, 10, 15, 20, 30, 40 min.). The test compound is usually dissolved in DMSO. The DMSO concentration in the incubation mixture is usually 0.1% or less since more solvent can drastically reduce the activities of some CYP450s. Incubations are done in 100 mM potassium phosphate buffer, pH 7.4 and at 37° C. Acetonitrile or methanol is used to stop the reaction. The parent compound is analysed by HPLC-MS. From the calculated half-life, $t_{1/2}$, the intrinsic clearance, Clint, is estimated by taking microsomal protein concentration and liver weight into account.

In general, the compounds of the invention had in vitro metabolic stability at a high level. Intrinsic clearance values tested as above were generally lower than 40 μl/min/mg protein.

The following table illustrates the properties of the compounds of the present invention:

3-Bromo-N-((2S)-2-(4-fluorophenyl)-4-{3-[(8aR)-6-oxo-hexahydropyrrolo[1,2-a]pyrazin-2(1H)-yl]azetidin-1-yl}butyl)-N-methyl-5-(trifluoromethyl)benzamide dihydrochloride (Ex 1)

| pKB (NK1) | pKB (NK2) | pKB (NK3) | $IC_{50}$ (hERG) | $IC_{50}$ (CYP3A4) | CLint (HLM) |
|---|---|---|---|---|---|
| 8.7 | 7.8 | 8.5 | 12.4 μM | >50 μM | 14.0 μL/min/mg |

Biological Evaluation

Gerbil Foot Tap (NK1 Specific Test Model)

Male Mongolian gerbils (60-80 g) are purchased from Charles River, Germany. On arrival, they are housed in groups of ten, with food and water ad libitum in temperature and humidity-controlled holding rooms. The animals are allowed at least 7 days to acclimatize to the housing conditions before experiments. Each animal is used only once and euthanized immediately after the experiment by heart punctuation or a lethal overdose of penthobarbital sodium.

Gerbils are anaesthetized with isoflurane. Potential CNS-permeable NK1 receptor antagonists are administered intraperitoneally, intravenously or subcutaneously. The compounds are given at various time points (typically 30-120 minutes) prior to stimulation with agonist.

The gerbils are lightly anaesthetized using isofluorane and a small incision is made in the skin over bregma. 10 pmol of ASMSP, a selective NK1 receptor agonist, is administered icv in a volume of 5 µl using a Hamilton syringe with a needle 4 mm long. The wound is clamped shut and the animal is placed in a small plastic cage and allowed to wake up. The cage is placed on a piece of plastic tubing filled with water and connected to a computer via a pressure transducer. The number of hind feet taps is recorded.

Fecal Pellet Output (NK2 Specific Test Model)

The in vivo effect (NK2) of the compounds of formula I can be determined by measuring NK2 receptor agonist-induced fecal pellet output using gerbil as described in e.g. The Journal of Pharmacology and Experimental Therapeutics (2001), pp. 559-564.

Colorectal Distension Model

Colorectal distension (CRD) in gerbils is performed as previously described in rats and mice (Tammpere A, Brusberg M, Axenborg J, Hirsch I, Larsson H, Lindström E. Evaluation of pseudo-affective responses to noxious colorectal distension in rats by manometric recordings. Pain 2005; 116: 220-226; Arvidsson S, Larsson M, Larsson H, Lindström E, Martinez V. Assessment of visceral pain-related pseudo-affective responses to colorectal distension in mice by intracolonic manometric recordings. J Pain 2006; 7: 108-118) with slight modifications. Briefly, gerbils are habituated to Bollmann cages 30-60 min per day for three consecutive days prior to experiments to reduce motion artefacts due to restraint stress. A 2 cm polyethylene balloon (made in-house) with connecting catheter is inserted in the distal colon, 2 cm from the base of the balloon to the anus, during light isoflurane anaesthesia (Forene®, Abbott Scandinavia AB, Solna, Sweden). The catheter is fixed to the tail with tape. The balloons are connected to pressure transducers (P-602, CFM-k33, 100 mmHg, Bronkhorst HI-TEC, Veenendal, The Netherlands). Gerbils are allowed to recover from sedation in the Bollmann cages for at least 15 min before the start of experiments.

A customized barostat (AstraZeneca, Mölndal, Sweden) is used to manage air inflation and balloon pressure control. A customized computer software (PharmLab on-line 4.0) running on a standard computer is used to control the barostat and to perform data collection. The distension paradigm used consists of 12 repeated phasic distensions at 80 mmHg, with a pulse duration of 30 sec at 5 min intervals. Compounds or their respective vehicle are administered as intraperitoneal (i.p.) injections before the CRD paradigm. Each gerbil receives both vehicle and compound on different occasions with at least two days between experiments. Hence, each gerbil serves as its own vehicle control.

The analog input channels are sampled with individual sampling rates, and digital filtering is performed on the signals. The balloon pressure signals are sampled at 50 samples/s. A highpass filter at 1 Hz is used to separate the contraction-induced pressure changes from the slow varying pressure generated by the barostat. A resistance in the airflow between the pressure generator and the pressure transducer further enhances the pressure variations induced by abdominal contractions of the animal. A customized computer software (PharmLab off-line 4.0) is used to quantify the magnitude of highpass-filtered balloon pressure signals. The average rectified value (ARV) of the highpass-filtered balloon pressure signals is calculated for 30 s before the pulse (i.e. baseline response) and for the duration of the pulse. When calculating the magnitude of the highpass-filtered balloon pressure signals, the first and last seconds of each pulse are excluded since these reflect artifact signals produced by the barostat during inflation and deflation and do not originate from the animal.

Methods of Preparation

In another aspect the present invention provides a process for preparing a compound of the formula (I) or salts thereof which process comprises:

a) reacting a compound of the formula (III) with a compound of the formula (IV):

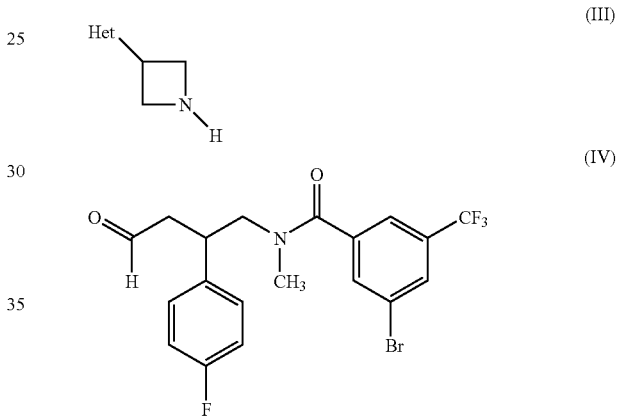

wherein Het is as hereinbefore defined; and the conditions are such that reductive alkylation of the compounds of the formula (III) forms an N—C bond between the nitrogen atom of the azetidine group of the compounds of formula (III) and the carbon atom of the aldehyde group of the compounds of formula (IV); or b) reacting a compound of the formula (III) with a compound of the formula (V):

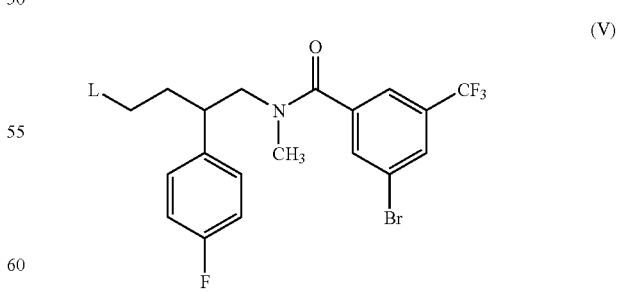

wherein Het is as hereinbefore defined; and L is a group such that alkylation of the compounds of the formula (III) forms an N—C bond between the nitrogen atom of the azetidine group of the compounds of formula (III) and the carbon atom of the compounds of formula (V) that is adjacent to the L group; or c) reacting a compound of the formula (VI) with a compound of the formula (VII):

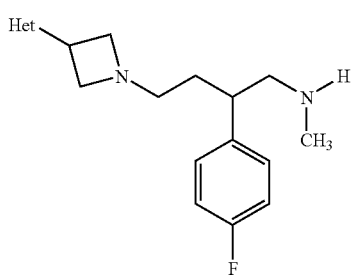

(VI)

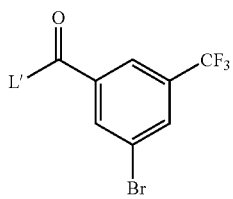

(VII)

wherein Het is as hereinbefore defined; and L' is a leaving group;
wherein any other functional group is protected, if necessary, and:
i) removing any protecting groups;
ii) optionally forming a pharmaceutically acceptable salt.

Protecting groups may in general be chosen from any of the groups described in the literature or known to the skilled chemist as appropriate for the protection of the group in question, and may be introduced and removed by conventional methods; see for example Protecting Groups in Organic Chemistry; Theodora W. Greene. Methods of removal are chosen so as to effect removal of the protecting group with minimum disturbance of groups elsewhere in the molecule.

The compounds of the formula (III) and (IV) are reacted under conditions of reductive alkylation. The reaction is typically performed at a non-extreme temperature, for example 0-40° C., in a substantially inert solvent for example dichloromethane. Typical reducing is agents include borohydrides such as sodium cyanoborohydride.

The compounds of the formula (III) and (V) are reacted under conditions of alkylation. Typically in the compounds of the formula (V) L is a leaving group such as halogen or alkylsulfonyloxy. The reaction is typically performed at an elevated temperature, for example 30-130° C., in a substantially inert solvent for example DMF.

The compounds of the formula (III) are known or may be prepared in conventional manner. The compound of the formula (IV) may be prepared, for example, by reacting a compound of the formula (VII) with a compound of the formula (VIII):

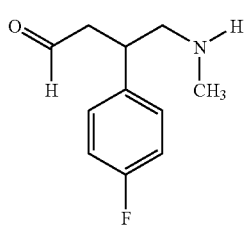

(VIII)

under conventional acylation conditions.

The compounds of the formula (V) may be prepared, for example, by reacting a compound of the formula (VII) with a compound of the formula (IX):

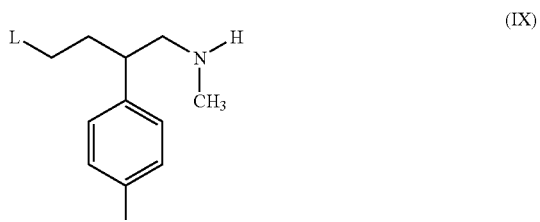

(IX)

wherein L is as hereinbefore defined, under conventional acylation conditions.

The compounds of the formulae (VI) and (VII) may be reacted under conventional acylation conditions wherein

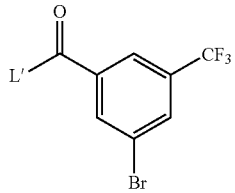

is an acid or an activated acid derivative. Such activated acid derivatives are well known in the literature. They may be formed in situ from the acid or they may be prepared, isolated and subsequently reacted. Typically L' is chloro thereby forming the acid chloride. Typically the acylation reaction is performed in the presence of a non-nucleophilic base, for example N,N-diisopropylethylamine, in a substantially inert solvent such as dichloromethane at a non-extreme temperature.

The compounds of the formula (VIII) and (IX) are known or may be prepared in conventional manner.

EXAMPLES

Working Examples

It should be emphasised that the compounds of the present invention most often show highly complex NMR spectra due to the existence of conformational isomers. This is believed to be a result from slow rotation about the amide and/or aryl bond. The following abbreviations are used in the presentation of the NMR data of the compounds: s-singlet; d-doublet; t-triplet; qt-quartet; qn-quintet; m-multiplet; b-broad; cm-complex multiplet, which may include broad peaks.

The following examples will describe, but not limit, the invention.

The following abbreviations are used in the experimental: Boc (tert-butoxycarbonyl), DIPEA (N,N-diisopropylethylamine), DMF (N,N-dimethylformamide), TBTU (N,N,N', N'-tetramethyl-O-(benzotriazol-1-yl)uronium tetrafluoroborate), THF (tetrahydrofuran), IPA (2-propanol) and RT (room temperature).

Example 1

3-Bromo-N-((2S)-2-(4-fluorophenyl)-4-{3-[(8aR)-6-oxohexahydropyrrolo[1,2-a]pyrazin-2(1H)-yl]azetidin-1-yl}butyl)-N-methyl-5-(trifluoromethyl)benzamide dihydrochloride

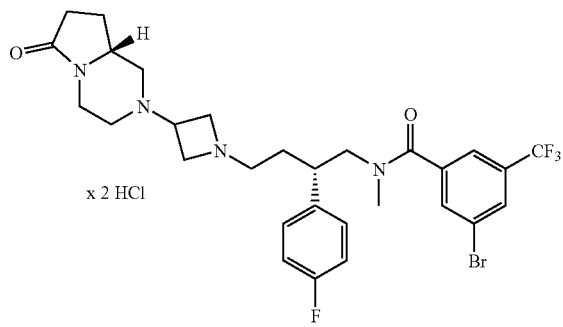

To a solution of 3-bromo-N-[(2S)-2-(4-fluorophenyl)-4-oxobutyl]-N-methyl-5-(trifluoromethyl)benzamide (see Method 3; 106 mg, 0.24 mmol) and (8aR)-2-azetidin-3-yl-hexahydropyrrolo[1,2-a]pyrazin-6(2H)-one (see Method 1; 35 mg, 0.18 mmol) in methanol (7 mL) was added a mixture of sodium cyano borohydride (73 mg, 1.2 mmol), zinc chloride (77 mg, 0.56 mmol) in a small amount of methanol. The reaction mixture was stirred at RT for 15 min and then the solvent was removed by evaporation. The residue was partitioned between ethyl acetate and aqueous NaHCO$_3$ and then the aqueous solution was separated and extracted once more with ethyl acetate. The solvent was removed by evaporation. The product was purified by means of reversed phase chromatography using a mixture of acetonitrile and aqueous 0.1 M ammonium acetate. The proper fractions were combined and concentrated on a rotavapor. The aqueous residue was extracted with ethyl acetate and the organic solution was dried over MgSO$_4$. The solvent was removed by evaporation and the residue was then dissolved in a small amount of water. A few drops of diluted hydrochloric acid were added and the solvent was removed by freeze-drying. There was obtained 68 mg (54%) of the title compound as a white powder. $^1$H NMR (500 MHz, CDCl$_3$): 1.7-4.8 (cm, 26H), 7.0-8.0 (cm, 7H); LCMS: m/z 626 (M+1)$^+$.

Example 2

3-Bromo-N-((2S)-2-(4-fluorophenyl)-4-{3-[(8aS)-6-oxohexahydropyrrolo[1,2-a]pyrazin-2(1H)-yl]azetidin-1-yl}butyl)-N-methyl-5-(trifluoromethyl)benzamide dihydrochloride

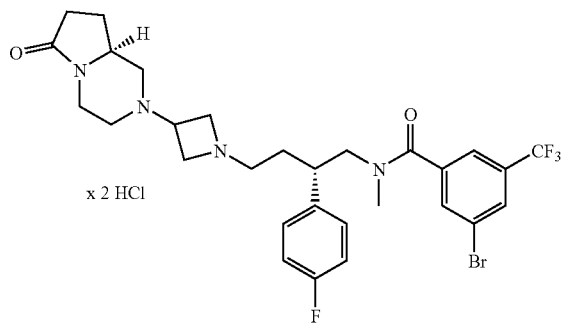

The title compound was prepared by utilizing the same reductive alkylation protocol as described in Example 1 but using (8aR)-2-azetidin-3-ylhexahydropyrrolo[1,2-a]pyrazin-6(2H)-one (see Method 2) as the amine (yield, 37%). $^1$H NMR (500 MHz, CDCl$_3$): 1.7-4.9 (cm, 26H), 7.0-8.0 (cm, 7H); LCMS: m/z 626 (M+1)$^+$.

Example 3

3-Bromo-N-{(2S)-2-(4-fluorophenyl)-4-[3-(6-oxooctahydro-2H-pyrido[1,2-a]pyrazin-2-yl)azetidin-1-yl]butyl}-N-methyl-5-(trifluoromethyl)benzamide dihydrochloride

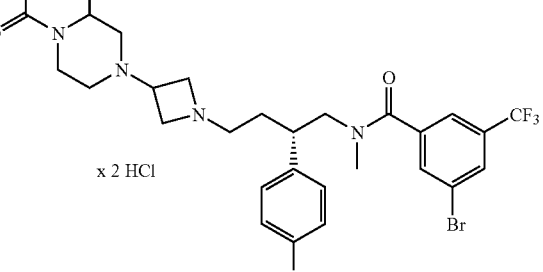

To a solution of 3-bromo-N-[(2S)-2-(4-fluorophenyl)-4-oxobutyl]-N-methyl-5-(trifluoromethyl)benzamide (see Method 3; 100 mg, 0.22 mmol) and 2-azetidin-3-yloctahydro-6H-pyrido[1,2-a]pyrazin-6-one (see Method 4; 58 mg, 0.28 mmol) in methylene chloride (3 mL) were added DIPEA (116 mg, 0.90 mmol) and sodium triacetoxyborohydride (66 mg, 0.31 mmol). The reaction mixture was stirred under nitrogen at RT for 2 h. The solution was washed twice with aqueous NaHCO$_3$ and the organic solvent dried by a phase separator column. The solvent was removed by evaporation and the product was purified by chromatography on silica gel (ammonia saturated methanol-methylene chloride 1% to 10%). The right fractions were combined and concentrated on a rotavapor and the residue was then dissolved in a small amount of acetonitrile/water. A few drops of diluted hydrochloric acid were added and the water was removed by freeze-drying. There was obtained 114 mg (70%) of the title compound as a white solid. $^1$H NMR (500 MHz, CDCl$_3$): 1.4-3.8 (cm, 27H), 4.6 (d, 1H), 6.8-7.4 (cm, 6H), 7.7 (s, 1H); LCMS: m/z 640 (M+1)$^+$.

Example 4

3-Bromo-N-((2S)-2-(4-fluorophenyl)-4-{3-[(9aR or 9aS)-6-oxooctahydro-2H-pyrido[1,2-a]pyrazin-2-yl]azetidin-1-yl}butyl)-N-methyl-5-(trifluoromethyl)benzamide

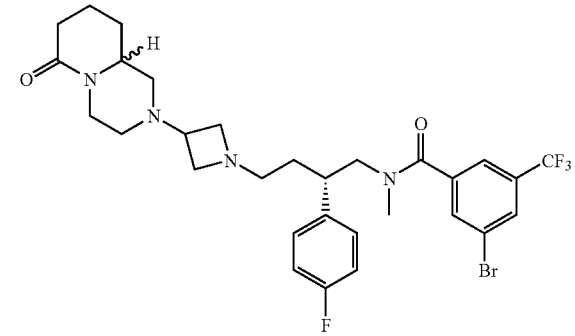

To a solution of 3-bromo-N-[(2S)-2-(4-fluorophenyl)-4-oxobutyl]-N-methyl-5-(trifluoromethyl)benzamide (see Method 3; 267 mg, 0.30 mmol) and one of the enantiomers of 2-azetidin-3-yloctahydro-6H-pyrido[1,2-a]pyrazin-6-one described in Method 5 (74 mg, 0.35 mmol) in methylene chloride (3 mL) were added DIPEA (150 mg, 1.15 mmol) and sodium triacetoxyborohydride (86 mg, 0.41 mmol). The reaction mixture was stirred under nitrogen at RT for 2.5 h. The solution was washed twice with aqueous NaHCO₃ and the organic solvent dried by a phase separator column. The solvent was removed by evaporation and the product was purified by chromatography on silica gel (ammonia saturated methanol-methylene chloride 1% to 10%). The right fractions were combined and the solvent was removed by evaporation. There was obtained 133 mg (68%) of the title compound as a white foam. $^1$H NMR (400 MHz, CDCl₃): 1.2-3.8 (cm, 27H), 4.6 (d, 1H), 6.7-7.4 (cm, 6H), 7.7 (s, 1H); LCMS: m/z 640 (M+1)⁺.

Example 5

3-Bromo-N-((2S)-2-(4-fluorophenyl)-4-{3-[(9aR or 9aS)-6-oxooctahydro-2H-pyrido[1,2-a]pyrazin-2-yl] azetidin-1-yl}butyl)-N-methyl-5-(trifluoromethyl) benzamide

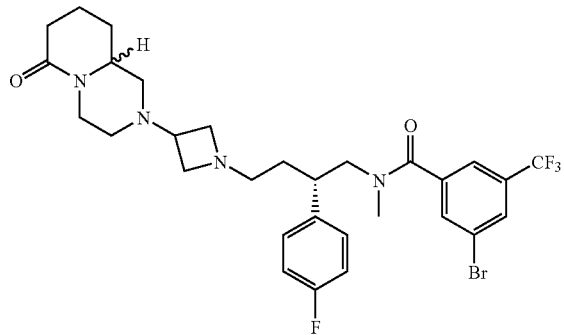

The title compound was prepared by utilizing the same reductive alkylation protocol as described in Example 4 but using the opposite enantiomer of 2-azetidin-3-yloctahydro-6H-pyrido[1,2-a]pyrazin-6-one described in Method 6 as the amine (yield, 67%). $^1$H NMR (400 MHz, CDCl₃): 1.2-3.8 (cm, 27H), 4.5-4.6 (d, 1H), 6.7-7.4 (cm, 6H), 7.7 (s, 1H); LCMS: m/z 640 (M+1)⁺.

Example 6

3-Bromo-N-{(2S)-2-(4-fluorophenyl)-4-[3-(4-acetylpiperazin-1-yl)azetidin-1-yl]butyl}-N-methyl-5-(trifluoromethyl)benzamide

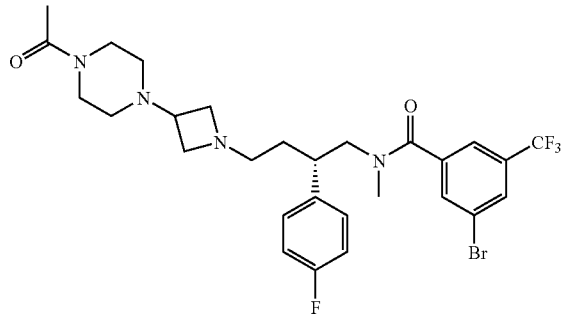

3-Bromo-N-[(2S)-2-(4-fluorophenyl)-4-oxobutyl]-N-methyl-5-(trifluoromethyl)benzamide (see Method 3; 11.2 g, 25 mmol) was dissolved in methanol (50 mL) together with triethylamine (3.5 mL, 25 mmol). Together with another portion of triethylamine (3.5 mL, 25 mmol) the solution was transferred to a flask containing 1-acetyl-4-azetidin-3-ylpiperazine dihydrochloride (see WO 96/05193; 8.4 g, 32.6 mmol). The mixture was stirred at RT for 45 min and then sodium triacetoxyborohydride (8.0 g, 37.6 mmol) was added by installments during one hour. The reaction mixture was stirred at RT for 45 min. Water (0.45 mL) was added and then most of the solvent was removed by evaporation. The residue was dissolved in toluene (56 mL) and then an aqueous 10% solution of NaOH (55 mL) was added while heating to 40° C. The mixture was stirred vigorously at 45° C. for 5 min. The aqueous layer was separated off and the organic solution was left in the hood overnight. After several attempts to crystallize the product from different solvents the compound was purified by means of silica gel chromatography (ammonia saturated methanol-methylene chloride 1% to 10%). There was obtained 8.3 g (54%) of the title compound as a white foam. $^1$H NMR (500 MHz, CDCl₃): 1.4-1.8 (cm, 2H), 2.0 (s, 3H), 2.1-3.8 (cm, 21H), 6.8-7.4 (cm, 6H), 7.7 (s, 1H); LCMS: m/z 614 (M+1)⁺.

Example 7

3-Bromo-N-{(2S)-2-(4-fluorophenyl)-4-[3-(4-propionylpiperazin-1-yl)azetidin-1-yl]butyl}-N-methyl-5-(trifluoromethyl)benzamide dihydrochloride

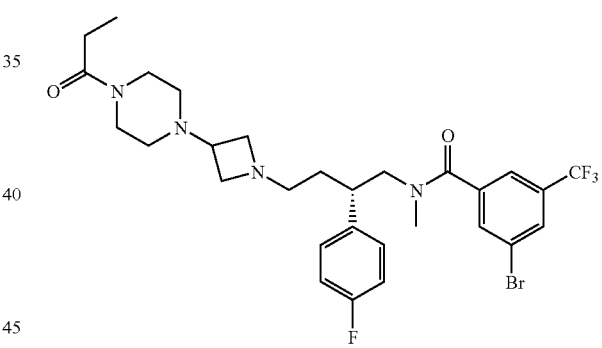

3-Bromo-N-[(2S)-2-(4-fluorophenyl)-4-oxobutyl]-N-methyl-5-(trifluoromethyl)benzamide (see Method 3; 165 mg, 0.4 mmol) and 1-azetidin-3-yl-4-propionylpiperazine (see Method 7; 80 mg, 0.41 mmol) were dissolved in methylene chloride (10 mL) together with a small amount of dry methanol (0.2 mL). Sodium triacetoxyborohydride (157 mg, 0.74 mmol) was added together with DIPEA (143 mg, 1.11 mmol). The reaction mixture was stirred at RT for 2.5 h and then diluted with methylene chloride. The solution was washed twice with aqueous NaHCO₃ and then with brine. The organic phase was separated by means of a phase separator column and then the solvent was removed by evaporation. The product was purified by chromatography on silica gel (methanol-methylene chloride 5:95). The oily product was dissolved in 2M hydrochloric acid and the solvent was then removed by freeze-drying. There was obtained 120 mg (48%) of the title compound as a white solid. $^1$H NMR (500 MHz, CDCl₃): 1.2-3.8 (cm, 28H), 6.8-7.8 (cm, 7H); LCMS: m/z 628 (M+1)⁺.

Example 8

3-Bromo-N-{(2S)-2-(4-fluorophenyl)-4-[3-(4-oxo-hexahydropyrazino[2,1-c][1,4]oxazin-8(1H)-yl)azetidin-1-yl]butyl}-N-methyl-5-(trifluoromethyl)benzamide

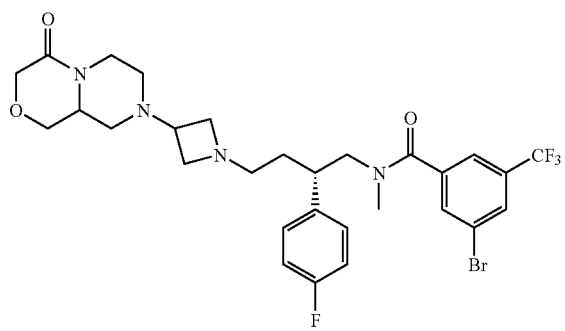

8-Azetidin-3-ylhexahydropyrazino[2,1-c][1,4]oxazin-4(3H)-one hydrochloride (see Method 8; 43 mg, 0.17 mmol) was dissolved in methanol (3 mL) together with a few drops of water and acetic acid (0.2 mL). 3-Bromo-N-[(2S)-2-(4-fluorophenyl)-4-oxobutyl]-N-methyl-5-(trifluoromethyl)benzamide (see Method 3; 80 mg, 0.18 mmol) dissolved in methanol (1 mL) was added to the former solution together with (polystyrylmethyl)-trimethylammonium cyanoborohydride (4.2 mmol/g, 47 mg, 0.25 mmol). The reaction mixture was heated to 120° C. for 5 min using microwave single node heating. The resin was filtered off and washed with methanol. The filtrate was concentrated by evaporation. The product was purified by reversed phase chromatography (acetonitrile-aqueous solution of ammonium formate 0.1M and formic acid 0.1M, 10% to 50%). The solvent of the collected fractions was removed by evaporation followed by freeze-drying. The residue was partitioned between methylene chloride and aqueous NaHCO$_3$. The two phases were separated by means of a phase separator column and then the solvent of the organic solution was removed by evaporation. There was obtained 50 mg (44%) of the title compound. $^1$H NMR (500 MHz, CD$_3$OD): 1.5-1.7 (b, 1H), 1.7-2.0 (cm, 3H), 2.2-4.2 (cm, 21H), 4.5 (d, 1H), 7.0-7.6 (cm, 6H), 7.9 (d, 1H); LCMS: m/z 642 (M+1)$^+$.

Example 9

3-Bromo-N-((2S)-2(4-fluorophenyl)-4-{3-[4-(tetrahydrofuran-2-ylcarbonyl)piperazin-1-yl]azetidin-1-yl}butyl)-N-methyl-5-(trifluoromethyl)benzamide

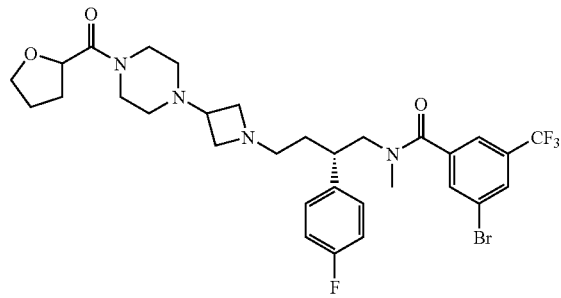

The title compound was prepared by utilizing the same reductive alkylation protocol as described in Example 8 but using 1-azetidin-3-yl-4-(tetrahydrofuran-2-ylcarbonyl)piperazine (see Method 9) as the amine (yield, 60%). $^1$H NMR (500 MHz, CD$_3$OD): 1.5-4.9 (cm, 30H), 7.0-8.0 (cm, 7H); LCMS: m/z 670 (M+1)$^+$.

Example 10

3-Bromo-N-((2S)-2-(4-fluorophenyl)-4-{3-[4-(methoxyacetyl)piperazin-1-yl]azetidin-1-yl}butyl)-N-methyl-5-(trifluoromethyl)benzamide

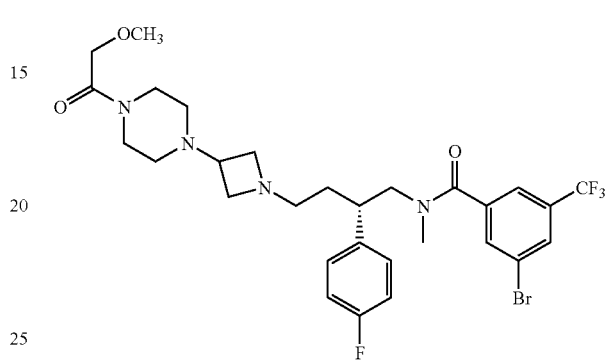

The title compound was prepared by utilizing the same reductive alkylation protocol as described in Example 8 but using 1-azetidin-3-yl-4-(methoxyacetyl)piperazine (see Method 10) as the amine (yield, 68%). $^1$H NMR (500 MHz, CD$_3$OD): 1.5-1.9 (cm, 2H), 2.2-3.6 (cm, 22H), 3.7 (m, 1H), 3.9 (t, 1H), 4.2 (s, 2H), 7.0 (d, 2H), 7.1 (t, 1H), 7.2-7.3 (d, 1H), 7.3-7.6 (m, 2H), 7.9 (d, 1H); LCMS: m/z 644 (M+1)$^+$.

Example 11

3-Bromo-N-{(2S)-2-(4-fluorophenyl)-4-[3-(4-glycoloylpiperazin-1-yl)azetidin-1-yl]butyl}-N-methyl-5-(trifluoromethyl)benzamide

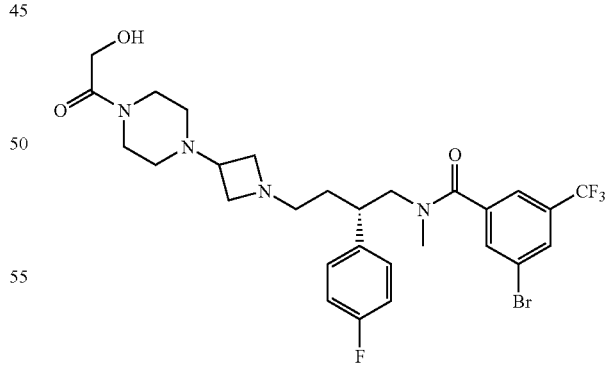

The title compound was prepared by utilizing the same reductive alkylation protocol as described in Example 8 but using 2-(4-azetidin-3-ylpiperazin-1-yl)-2-oxoethanol (see Method 11) as the amine (yield, 50%). $^1$H NMR (500 MHz, CD$_3$OD): 1.6-1.9 (cm, 2H), 2.2-3.6 (cm, 19H), 3.7 (m, 1H), 3.9 (m, 1H), 4.2 (s, 2H), 7.0-7.6 (m, 6H), 7.9 (d, 1H); LCMS: m/z 630 (M+1)$^+$.

Example 12

3-Bromo-N-((2S)-2-(4-fluorophenyl)-4-{3-[(9aS)-4-oxohexahydropyrazino[2,1-c][1,4]oxazin-8(1H)-yl]azetidin-1-yl}butyl)-N-methyl-5-(trifluoromethyl)benzamide

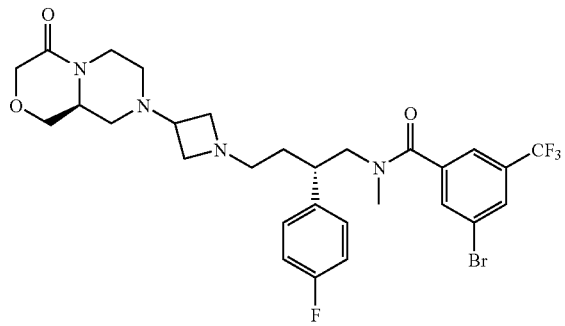

To a solution of 3-bromo-N-[(2S)-2-(4-fluorophenyl)-4-oxobutyl]-N-methyl-5-(trifluoromethyl)benzamide (see Method 3; 100 mg, 0.22 mmol) and (9aS)-8-azetidin-3-yl-hexahydropyrazino[2,1-c][1,4]oxazin-4(3H)-one (see Method 12; ~0.20 mmol) in ethanol (20 mL) was added a solution of sodium cyano borohydride (125 mg, 2.0 mmol) and zinc chloride (135 mg, 0.99 mmol) in methanol (10 mL). The reaction mixture was stirred at RT for 10 min and then the solvent was removed by evaporation. The residue was partitioned between ethyl acetate (50 mL) and water (20 mL). The organic solution was washed with brine and then dried over $Na_2SO_4$. The solvent was removed by evaporation and the residue was dissolved in a mixture of acetonitrile (10 mL), acetic acid (100 mg) and water (20 mL). The product was purified by means of reversed phase chromatography using a mixture of acetonitrile and aqueous 0.1 M ammonium acetate. The proper fractions were combined and concentrated on a rotavapor. The aqueous residue was extracted with ethyl acetate and the organic solution was dried over $Na_2SO_4$. The solvent was removed by evaporation. There was obtained 80 mg (55%) of the title compound. $^1$H NMR (400 MHz, $CDCl_3$): 0.9-3.8 (cm, 21.5H), 3.9 (d, 1H), 4.1-4.2 (qt, 2H), 4.4 (b, 0.5H), 4.5-4.6 (d, 1H), 6.6-7.5 (cm, 6H), 7.8 (s, 1H); LCMS: m/z 642 (M+1)$^+$.

Example 13

3-Bromo-N-((2S)-2-(4-fluorophenyl)-4-{3-[(9aR)-4-oxohexahydropyrazino[2,1-c][1,4]oxazin-8(1H)-yl]azetidin-1-yl}butyl)-N-methyl-5-(trifluoromethyl)benzamide

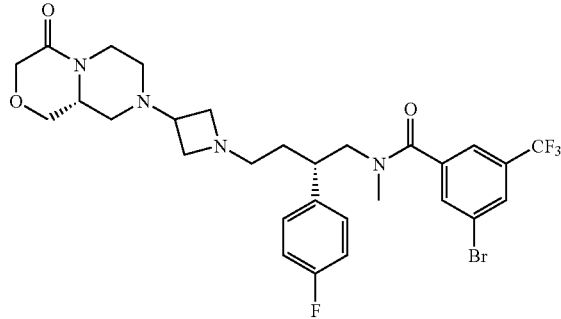

The title compound was prepared by utilizing the same reductive alkylation reaction protocol as described in Example 12 but using (9aR)-8-azetidin-3-ylhexahydropyrazino[2,1-c][1,4]oxazin-4(3H)-one (see Method 13) as the amine (yield, 40%). $^1$H NMR (400 MHz, $CDCl_3$): 0.9-3.8 (cm, 21.7H), 3.9 (dd, 1H), 4.0-4.2 (qt, 2H), 4.3-4.4 (b, 0.3H), 4.5-4.6 (d, 1H), 6.8-7.4 (cm, 6H), 7.7 (s, 1H); LCMS: m/z 642 (M+1)$^+$.

Example 14

3-Bromo-N-[(2S)-4-{3-[4-(cyclopropylcarbonyl)piperazin-1-yl]azetidin-1-yl}-2-(4-fluorophenyl)butyl]-N-methyl-5-(trifluoromethyl)benzamide dihydrochloride

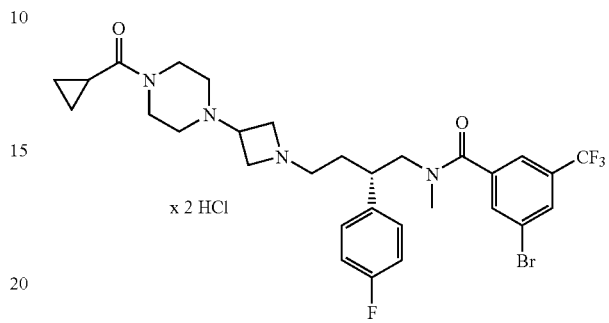

To a solution of 3-bromo-N-[(2S)-2-(4-fluorophenyl)-4-oxobutyl]-N-methyl-5-(trifluoromethyl)benzamide (see Method 3; 450 mg, 1.0 mmol) and 1-azetidin-3-yl-4-(cyclopropylcarbonyl)piperazine (see Method 14; ~0.9 mmol) in methanol (50 mL) was added a solution of sodium cyano borohydride (250 mg, 4.0 mmol) and zinc chloride (270 mg, 2.0 mmol) in methanol (30 mL). The reaction mixture was stirred at RT for 15 min and then the solvent was removed by evaporation. The residue was partitioned between ethyl acetate (50 mL) and water (20 mL). The organic solution was washed with brine and then dried over $Na_2SO_4$. The solvent was removed by evaporation and the residue was dissolved in ethyl acetate. The product was purified by means of silica gel chromatography first eluting with ethyl acetate and then with a mixture of ethyl acetate, methanol and triethylamine (9:1:1). The proper fractions were combined and concentrated on a rotavapor and then the residue was co-evaporated twice using methylene chloride. The residue was dissolved in methylene chloride and to the solution was added HCl-saturated diethyl ether (1 mL). The solvent was removed by evaporation and then the residue was co-evaporated twice with methylene chloride. There was obtained 220 mg (30%) of the title compound. $^1$H NMR (400 MHz, $CDCl_3$): 0.8-1.0 (cm, 4H), 1.2-4.7 (cm, 24H), 6.9-8.0 (cm, 7H): m/z 640 (M+1)$^+$.

Example 15

3-Bromo-N-[(2S)-4-[3-(4-butyrylpiperazin-1-yl)azetidin-1-yl]-2-(4-fluorophenyl)butyl]-N-methyl-5-(trifluoromethyl)benzamide dihydrochloride

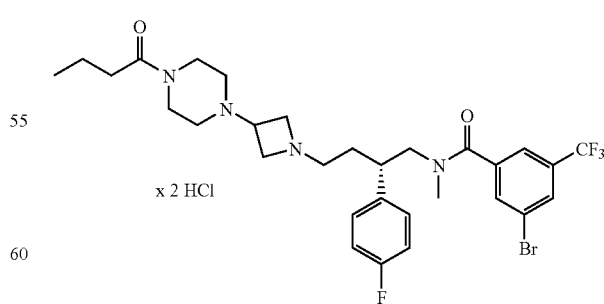

To a solution of 3-bromo-N-[(2S)-2-(4-fluorophenyl)-4-oxobutyl]-N-methyl-5-(trifluoromethyl)benzamide (see Method 3; 450 mg, 1.0 mmol) and 1-azetidin-3-yl-4-(cyclopropylcarbonyl)piperazine (see Method 15; ~0.9 mmol) in methanol (50 mL) was added a solution of sodium cyano borohydride (250 mg, 4.0 mmol) and zinc chloride (270 mg, 2.0 mmol) in methanol (30 mL). The reaction mixture was stirred at RT for 15 min and then the solvent was removed by evaporation. The residue was partitioned between ethyl acetate (50 mL) and water (20 mL). The organic solution was washed with brine and then dried over Na$_2$SO$_4$. The solvent was removed by evaporation and the residue was dissolved in ethyl acetate. The product was purified by means of silica gel chromatography first eluting with ethyl acetate and then with a mixture of ethyl acetate, methanol and triethylamine (9:1:1). The proper fractions were combined and concentrated on a rotavapor then the residue was co-evaporated twice using methylene chloride. The residue was dissolved in methylene chloride and to the solution was added HCl-saturated diethyl ether (1 mL). The solvent was removed by evaporation and then, the residue was co-evaporated twice with methylene chloride. There was obtained 220 mg (30%) of the title compound. $^1$H NMR (400 MHz, CD$_3$OD): 0.8-1.0 (t, 3H), 1.5-1.6 (qt, 2H), 1.8-2.2 (cm, 3H), 2.4 (t, 2H), 2.6-4.6 (cm, 20H), 7.0-7.6 (cm, 6H), 7.9 (d, 1H); LCMS: m/z 642 (M+1)$^+$.

Example 16

3-Bromo-N-{(2S)-2-(4-fluorophenyl)-4-[3-(4-isobutyrylpiperazin-1-yl)azetidin-1-yl]butyl}-N-methyl-5-(trifluoromethyl)benzamide dihydrochloride

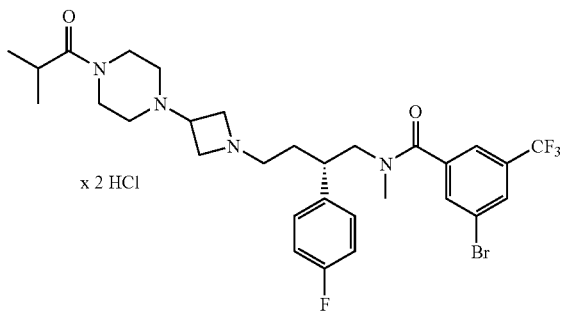

The title compound was prepared by utilizing the same reductive alkylation reaction protocol as described in Example 15 but using 1-azetidin-3-yl-4-isobutyrylpiperazine (see Method 16) as the amine (yield, 29%). $^1$H NMR (400 MHz, CD$_3$OD): 1.1 (d, 6H), 1.8-2.2 (cm, 3H), 2.6-4.6 (cm, 21H), 6.8-7.6 (cm, 6H), 7.9 (d, 1H); LCMS: m/z 642 (M+1)$^+$.

Preparation of Starting Materials

The starting materials for the examples above are either commercially available or are readily prepared by standard methods from known materials. For example, the following reactions are an illustration, but not a limitation, of some of the starting materials.

Method 1

(8aR)-2-Azetidin-3-ylhexahydropyrrolo[1,2-a]pyrazin-6(2H)-one

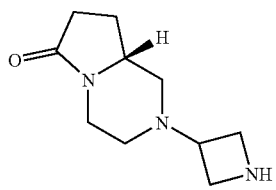

(a) (8aR)-2-[1-(Diphenylmethyl)azetidin-3-yl]hexahydropyrrolo[1,2-a]pyrazin-6(2H)-one (8aR)-Hexahydropyrrolo[1,2-a]pyrazin-6(2H)-one (see WO 03/066635; 0.17 g, 1.2 mmol), 1-(diphenylmethyl)azetidin-3-yl methanesulfonate (see J. Org. Chem.; 56; 1991; 6729; 0.40 g, 1.3 mmol) and triethylamine (0.20 mL, 1.4 mmol) were dissolved in acetonitrile. The mixture was heated for 15 min at 150° C. using microwave single node heating and then the solvent was removed by evaporation. The residue was partitioned between ethyl acetate and aqueous NaHCO$_3$ and the aqueous phase extracted further with ethyl acetate. The organic phase was dried and then the solvent was removed by evaporation. The product was purified by chromatography on silica gel (methanol-methylene chloride 5:95). There was obtained 0.23 g (54%) of (8aR)-2-[1-(diphenylmethyl)azetidin-3-yl]hexahydropyrrolo[1,2-a]pyrazin-6(2H)-one as a pale yellow oil. $^1$H NMR (500 MHz, CDCl$_3$): 1.5-1.6 (m, 2H), 1.7-1.8 (m, 1H), 2.1-2.2 (m, 1H), 2.3-2.4 (m, 2H), 2.6-2.7 (d, 1H), 2.8 (m, 1H), 2.8-2.9 (m, 3H), 3.0 (qn, 1H), 3.4 (t, 2H), 3.6 (m, 1H), 4.0 (d, 1H), 4.4 (s, 1H), 7.2 (m, 2H), 7.2-7.3 (m, 4H), 7.4 (m, 4H); LCMS: m/z 362 (M+1)$^+$.

(b) (8aR)-2-Azetidin-3-ylhexahydropyrrolo[1,2-a]pyrazin-6(2H)-one (8aR)-2-[1-(diphenylmethyl)azetidin-3-yl]hexahydropyrrolo[1,2-a]pyrazin-6(2H)-one (0.23 g, 0.64 mmol) was dissolved in acetic acid (20 mL) and to the resultant solution was added palladium hydroxide on carbon (0.33 g). The mixture was stirred under hydrogen (5 bar) at RT for 48 h and then the catalyst was filtered off by means of Celite®. The solvent was removed by evaporation and the residue was dissolved in ethanol. The solution was filtered through a cation exchange column (Isolute SCX-2, 10 g). The column was washed with ethanol and then the product was eluted with ammonia-saturated methanol. The solvent was removed by evaporation and there was obtained 0.10 g (84%) of the title compound. $^1$H NMR (500 MHz, CDCl$_3$): 1.5-1.6 (m, 2H), 1.8 (m, 1H), 2.1-2.2 (m, 1H), 2.3-2.4 (m, 2H), 2.7 (d, 1H), 2.8-2.9 (m, 2H), 3.2 (qn, 1H), 3.5-3.7 (m, 4H), 4.0 (dd, 1H).

Method 2

(8aS)-2-Azetidin-3-ylhexahydropyrrolo[1,2-a]pyrazin-6(2H)-one

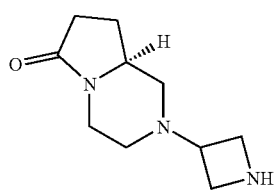

(a) (8aS)-2-[1-(Diphenylmethyl)azetidin-3-yl]hexahydropyrrolo[1,2-a]pyrazin-6(2H)-one The title compound was prepared by utilizing the N-alkylation reaction protocol described in Method 1a but using (8aS)-hexahydropyrrolo[1,2-a]pyrazin-6(2H)-one (see WO 03/066635) as the amine (yield, 56%). $^1$H NMR (500 MHz, CDCl$_3$): 1.5-1.6 (qn, 2H), 1.7-1.8 (m, 2H), 2.1-2.2 (m, 1H), 2.3-2.4 (m, 2H), 2.6-2.7 (d, 1H), 2.8 (d, 1H), 2.8-2.9 (m, 2H), 3.0 (qn, 1H), 3.4 (t, 2H), 3.6 (m, 1H), 4.0 (d, 1H), 4.4 (s, 1H), 7.1-7.2 (t, 2H), 7.2-7.3 (t, 4H), 7.4 (t, 4H); LCMS: m/z 362 (M+1)⁺.

(b) (8aS)-2-Azetidin-3-ylhexahydropyrrolo[1,2-a]pyrazin-6(2H)-one

The title compound was prepared by utilizing the hydrogenation reaction protocol described in Method 1b but using (8aS)-2-[1-(diphenylmethyl)azetidin-3-yl]hexahydropyrrolo[1,2-a]pyrazin-6(2H)-one as the substrate (yield, 73%). ¹H NMR (500 MHz, CDCl₃): 1.5-1.6 (m, 2H), 1.8 (m, 1H), 2.1-2.2 (m, 1H), 2.3-2.4 (m, 2H), 2.6-2.8 (d, 1H), 2.8-3.0 (m, 2H), 3.2-3.4 (m, 2H), 3.5-3.7 (m, 4H), 4.0 (dd, 1H).

Method 3

3-Bromo-N-[(2S)-2-(4-fluorophenyl)-4-oxobutyl]-N-methyl-5-(trifluoromethyl)benzamide

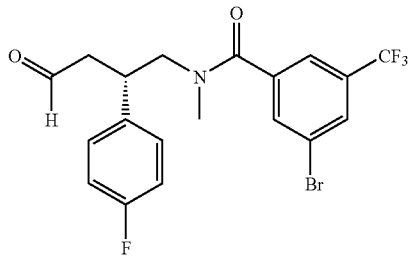

(a) 3-Bromo-N-[(2S)-2-(4-fluorophenyl)pent-4-en-1-yl]-N-methyl-5-(trifluoromethyl)benzamide To a solution of [(2S)-2-(4-fluorophenyl)pent-4-en-1-yl]methylamine (see *Bioorg. Med. Chem. Lett;* 2001; 265-270; 0.54 g, 2.8 mmol) and 3-bromo-5-trifluoromethyl benzoic acid (0.81 g, 3.0 mmol) in DMF (7 mL) was added TBTU (0.96 g, 3.0 mmol) and DIPEA (1.41 g, 10.9 mmol). The reaction mixture was stirred under nitrogen overnight at RT and then partitioned between ethyl acetate and an aqueous NaHCO₃ solution. The aqueous phase was extracted trice with ethyl acetate. The combined organic solutions were washed trice with water and then dried by a phase separator column. The solvent was removed by to evaporation and the product was purified by chromatography on silica gel (ethyl acetate-heptane 10% to 17%). There was obtained 0.86 g (68%) of 3-bromo-N-[(2S)-2-(4-fluorophenyl)pent-4-en-1-yl]-N-methyl-5-(trifluoromethyl)benzamide. ¹H NMR (500 MHz, CDCl₃): 2.1-3.8 (cm, 8H), 4.9-5.1 (m, 2H), 5.5-5.8 (m, 1H), 6.8-7.4 (cm, 6H), 7.8 (s, 1H).

(b) 3-Bromo-N-[(2S)-2-(4-fluorophenyl)-4-oxobutyl]-N-methyl-5-(trifluoromethyl)benzamide To a solution of 3-bromo-N-[(2S)-2-(4-fluorophenyl)pent-4-en-1-yl]-N-methyl-5-(trifluoromethyl)benzamide (0.86 g, 1.9 mmol) in acetone (45 mL) were added OsO₄ (2.5% in t-butyl alcohol, 0.49 mL, 0.039 mmol) and 4-methylmorpholine-4-oxide (0.41 g, 3.5 mmol). The solution was stirred under nitrogen at RT overnight and then an aqueous solution of NaHSO₃ (39%, 45 mL) was added. The mixture was stirred for 2 h, diluted with water and then extracted twice with methylene chloride. The combined organic solutions were separated by means of a phase separator column and the solvent was removed by evaporation. The residue (1.08 g) was dissolved in THF (18 mL) and water (4.5 mL) and to the resultant solution was added NaIO₄ (0.73 g, 3.4 mmol). The mixture was stirred under nitrogen overnight at RT. The mixture was partitioned between methylene chloride and water. The aqueous phase was extracted with methylene chloride and then the combined organic solutions were washed with brine and separated by means of a phase separator column. The solvent was removed by evaporation and there was obtained 0.78 g (90%) of the title compound. ¹H NMR (500 MHz, CDCl₃): 2.4-4.4 (cm, 8H), 6.8-7.8 (cm, 7H), 9.8 (s, 1H); LCMS: m/z 447 (M−1)⁺.

Method 4

2-Azetidin-3-yloctahydro-6H-pyrido[1,2-a]pyrazin-6-one

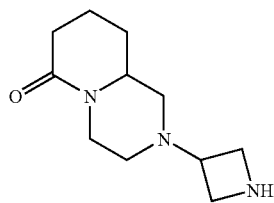

(a) 2-[1-(Diphenylmethyl)azetidin-3-yl]octahydro-6H-pyrido[1,2-a]pyrazin-6-one

To a solution of 1-(diphenylmethyl)azetidin-3-one (see *Bioorg. Med. Chem. Lett.;* 13; 2003; 2191-2194, 1.32 g, 5.6 mmol) and octahydro-6H-pyrido[1,2-a]pyrazin-6-one hydrochloride (see *Bioorg. Med. Chem.;* 2004; 71-86; 1.30 g, 6.8 mmol), in methanol (10 mL) was added acetic acid (1 mL). The solution was mixed with (polystyrylmethyl) trimethylammonium cyanoborohydride (4.2 mmol/g, 1.67 g, 8.8 mmol) and the mixture was heated for 5 min at 120° C. using microwave single node heating. The resin was filtered off and then the solvent was removed by evaporation. The product was purified by means of silica gel chromatography using a mixture of ammonia saturated methanol (2%) and methylene chloride. There was obtained 0.58 g (28%) of 2-[1-(diphenylmethyl)azetidin-3-yl]octahydro-6H-pyrido[1,2-a]pyrazin-6-one as an oil. ¹H NMR (500 MHz, CDCl₃): 1.4 (q, 1H), 1.7 (t, 2H), 1.8-2.0 (m, 3H), 2.3-2.4 (m, 1H), 2.4-2.5 (d, 1H), 2.7-2.8 (t, 3H), 3.0 (m, 3H), 3.4-3.6 (m, 3H), 4.5 (s, 1H), 4.6 (d, 1H), 7.2 (m, 2H), 7.3 (m, 4H), 7.4 (m, 4H); LCMS: m/z 376 (M+1)⁺.

(b) 2-Azetidin-3-yloctahydro-6H-pyrido[1,2-a]pyrazin-6-one

The title compound was prepared by utilizing the hydrogenation reaction protocol described in Method 1b but using (2-[1-(diphenylmethyl)azetidin-3-yl]octahydro-6H-pyrido[1,2-a]pyrazin-6-one as the substrate (yield, 99%). LCMS: m/z 210 (M+1)⁺.

Method 5

One of the enantiomers of 2-Azetidin-3-yloctahydro-6H-pyrido[1,2-a]pyrazin-6-one

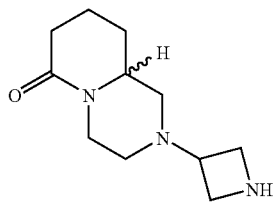

(a) (+)-2-[1-(Diphenylmethyl)azetidin-3-yl]octahydro-6H-pyrido[1,2-a]pyrazin-6-one The two enantiomers of 2-[1-(diphenylmethyl)azetidin-3-yl]octahydro-6H-pyrido[1,2-a]pyrazin-6-one (see Method 4a) were separated by means of chiral chromatography using Chiralcel® OD column (250×20 mm). Mobile phase was heptane/IPA/triethylamine (70/30/0.1) and injected amount was 160 mg. Sample concentration was 20 mg/mL in IPA. From 448 mg of the racemic compound there was obtained 134 mg of (+)-2-[1-(diphenylmethyl)azetidin-3-yl]octahydro-6H-pyrido[1,2-a]pyrazin-6-one with an optical purity of over 99.9% e.e. The sign of the optical rotation (+) was determined by measuring on line. LCMS: m/z 376 (M+1)$^+$.

(b) (+)-2-Azetidin-3-yloctahydro-6H-pyrido[1,2-a]pyrazin-6-one (+)-(2-[1-(Diphenylmethyl)azetidin-3-yl]octahydro-6H-pyrido[1,2-a]pyrazin-6-one (138 mg, 0.37 mmol) and ammonium formate (70 mg, 1.1 mmol) were dissolved in ethanol (3 mL). Palladium hydroxide on carbon (52 mg) was added and the reaction mixture was heated to 120° C. for 2 min using microwave single node heating. The catalyst was filtered off and the solvent was removed by evaporation. There was obtained 77 mg (100%) of the title compound. LCMS: m/z 210 (M+1)$^+$.

Method 6

The opposite enantiomer of 2-Azetidin-3-yloctahydro-6H-pyrido[1,2-a]pyrazin-6-one

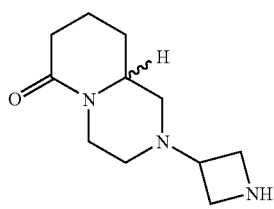

(a) (−)-2-[1-(Diphenylmethyl)azetidin-3-yl]octahydro-6H-pyrido[1,2-a]pyrazin-6-one The (−)-enantiomer of 2-[1-(diphenylmethyl)azetidin-3-yl]octahydro-6H-pyrido[1,2-a]pyrazin-6-one (see Method 4a) was isolated by means of chiral chromatography using conditions described in Method 5. From 448 mg of the racemic compound there was obtained 138 mg of (−)-2-[1-(diphenylmethyl)azetidin-3-yl]octahydro-6H-pyrido[1,2-a]pyrazin-6-one with an optical purity of over 99.9% e.e. The sign of the optical rotation (−) was determined by measuring on line. LCMS: m/z 376 (M+1)$^+$.

(b) The opposite enantiomer of 2-Azetidin-3-yloctahydro-6H-pyrido[1,2-a]pyrazin-6-one The title compound was prepared by utilizing the hydrogenation reaction protocol described in Method 5b but using (−)-(2-[1-(diphenylmethyl)azetidin-3-yl]octahydro-6H-pyrido[1,2-a]pyrazin-6-one as the substrate (yield, 100%). LCMS: m/z 210 (M+1)$^+$.

Method 7

1-Azetidin-3-yl-4-propionylpiperazine

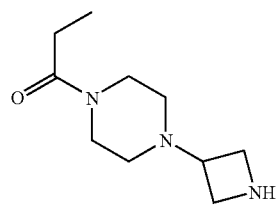

(a) 1-[1-(Diphenylmethyl)azetidin-3-yl]piperazine

A mixture of 1-(diphenylmethyl)azetidin-3-yl methanesulfonate (see *J. Org. Chem.*; 56; 1991; 6729; 25 g, 78.6 mmol), piperazine (67.7 g, 0.79 mol) and dry acetonitrile was stirred at 60° C. overnight under nitrogen. The mixture was cooled and partitioned between water and methylene chloride. The organic layer was washed with water and brine. The solution was dried over $Na_2SO_4$ and then the solvent was removed by evaporation. The residue was purified by column chromatography on silica gel (methanol-methylene chloride 5:95). There was obtained 17.5 g (72%) of 1-[1-(diphenylmethyl)azetidin-3-yl]piperazine as a yellow oil. $^1$H NMR (400 MHz, CDCl$_3$): 2.1-2.4 (m, 4H), 2.8-2.9 (m, 2H), 3.0 (m, 4H), 3.4-3.5 (m, 2H), 3.7-3.9 (m, 1H), 4.4 (s, 1H), 7.2-7.4 (m, 10H); LCMS: m/z 308 (M+1)$^+$.

(b) 1-[1-(Diphenylmethyl)azetidin-3-yl]-4-propionylpiperazine

A mixture of 1-[1-(diphenylmethyl)azetidin-3-yl]piperazine (250 mg, 0.81 mmol), $K_2CO_3$ (146 mg, 1.1 mmol), propionyl chloride (98 mg, 1.1 mmol) and acetonitrile (6 mL) was stirred at RT for 16 h. The mixture was filtered through a phase separator column and the solvent was removed by evaporation. The residue was dissolved in methylene chloride and the solution washed with aqueous NaHCO$_3$. The organic phase was separated by using a phase separator column and then the solvent was removed by evaporation. There was obtained 216 mg (73%) of 1-[1-(diphenylmethyl)azetidin-3-yl]-4-propionylpiperazine as an oil. $^1$H NMR (500 MHz, CDCl$_3$): 1.1-1.2 (t, 3H), 2.2-2.4 (m, 6H), 2.9 (t, 2H), 3.0 (m, 1H), 3.4-3.5 (m, 4H), 3.6 (b, 2H), 4.4 (s, 1H), 7.2 (m, 2H), 7.3 (m, 4H), 7.4 (m, 4H); LCMS: m/z 364 (M+1)$^+$.

(c) 1-Azetidin-3-yl-4-propionylpiperazine

1-[1-(diphenylmethyl)azetidin-3-yl]-4-propionylpiperazine (0.22 g, 0.59 mmol) was dissolved in a mixture of ethanol (9 mL) and acetic acid (0.2 mL) and to the resultant solution was added palladium hydroxide on carbon (83 mg). The mixture was stirred under hydrogen (5 bar) at RT for 23 h and then the catalyst was filtered off by means of a phase separator column then washing with ethanol. The solvent was removed by evaporation and the residue was dissolved in methanol (1 mL). The solution was filtered through a cation exchange column (Isolate SCX-2, 10 g). The column was washed with THF and then the product was eluted with ammonia-saturated methanol. The solvent was removed by evaporation and there was obtained 0.13 g (100%) of the title compound as an oil. $^1$H NMR (500 MHz, CD$_3$OD): 1.1 (t, 3H), 2.3-2.5 (m, 6H), 3.4 (m, 1H), 3.6 (m, 4H), 3.9-4.0 (m, 4H).

Method 8

8-Azetidin-3-ylhexahydropyrazino[2,1-c][1,4]oxazin-4(3H)-one hydrochloride

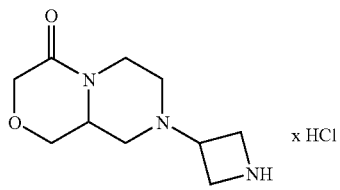

(a) tert-Butyl 4-oxohexahydropyrazino[2,1-c][1,4]oxazine-8(1H)-carboxylate

To a solution of tert-butyl 3-(hydroxymethyl)piperazine-1-carboxylate (360 mg, 1.7 mmol) in methylene chloride (10 mL) was added triethylamine (505 mg, 5.0 mmol) at 0° C. Chloroacetyl chloride (282 mg, 2.5 mmol) was dissolved in methylene chloride (5 mL) and the solution was added to the former solution drop by drop at 0° C. The reaction mixture was stirred at 0° C. for 1 h and then at RT for 3 h. An aqueous solution of KHSO$_4$ (1M, 5 mL) was added and then the organic phase was separated by means of a phase separator column. The solvent was removed by evaporation and the amide intermediate, which was purified by silica gel chromatography, was dissolved in DMF (2 mL). While cooling and under nitrogen the solution was added drop wise to a suspension of NaH (60 mg, 2.5 mmol) in DMF. The mixture was stirred at RT for 48 h, then diluted with ethyl acetate and then pored over aqueous HCl (0.5 M). The pH was adjusted to 12 with NaOH and then the organic phase was separated. The solvent was removed by evaporation and the product was purified by silica gel chromatography. There was obtained 90 mg (21%) of tert-butyl 4-oxohexahydropyrazino[2,1-c][1,4]oxazine-8(1H)-carboxylate. $^1$H NMR (500 MHz, CDCl$_3$): 1.4 (s, 9H), 2.5-2.7 (m, 2H), 2.8 (m, 1H), 3.4-3.5 (m, 2H), 3.9-4.2 (m, 5H), 4.5 (d, 1H); LCMS: m/z 257 (M+1)$^+$.

(b) Hexahydropyrazino[2,1-c][1,4]oxazin-4(3H)-one hydrochloride

To a solution of tert-butyl 4-oxohexahydropyrazino[2,1-c][1,4]oxazine-8(1H)-carboxylate (90 mg, 0.35 mmol) in acetonitrile (10 mL) was added concentrated aqueous HCl (3 drops). The mixture was stirred at RT for 30 min and then the solvent was removed by evaporation. There was obtained 74 mg (100%) of hexahydropyrazino[2,1-c][1,4]oxazin-4(3H)-one hydrochloride. $^1$H NMR (500 MHz, CD$_3$OD): 3.0-3.2 (m, 3H), 3.4-3.5 (m, 2H), 3.7-3.8 (m, 1H), 4.0 (m, 1H), 4.1 (m, 1H), 4.2 (s, 2H), 4.7-4.8 (m, 1H); LCMS: m/z 157 (M+1)$^+$.

(c) 8-[1-(Diphenylmethyl)azetidin-3-yl]hexahydropyrazino[2,1-c][1,4]oxazin-4(3H)-one The title compound was prepared by utilizing the reductive alkylation protocol described in Example 4a but using hexahydropyrazino[2,1-c][1,4]oxazin-4(3H)-one hydrochloride as the amine (yield, 54%). $^1$H NMR (500 MHz, CDCl$_3$): 1.7 (t, 1H), 1.8-1.9 (m, 1H), 2.6 (d, 1H), 2.7-2.8 (m, 2H), 2.9 (m, 2H), 3.0 (m, 1H), 3.4 (m, 2H), 3.5 (m, 1H), 3.6 (m, 1H), 3.9 (dd, 1H), 4.1-4.2 (m, 2H), 4.4 (s, 1H), 4.5-4.6 (d, 1H); LCMS: m/z 378 (M+1)$^+$.

(d) 8-Azetidin-3-ylhexahydropyrazino[2,1-c][1,4]oxazin-4(3H)-one hydrochloride

8-[1-(Diphenylmethyl)azetidin-3-yl]hexahydropyrazino[2,1-c][1,4]oxazin-4(3H)-one (84 mg, 0.22 mmol) was dissolved in a mixture of ethanol (4 mL) and acetic acid (0.4 mL) and to the resultant solution was added a small amount of palladium hydroxide on carbon. The mixture was stirred under hydrogen (5 bar) at RT for 24 h and then the catalyst was filtered off by means of Celite®. The solvent was removed by evaporation and the residue was partitioned between toluene and aqueous HCl (0.1M). The aqueous solution was separated and the solvent was removed by freeze-drying. There was obtained 53 mg (96%) of the title compound. $^1$H NMR (500 MHz, D$_2$O): 3.0-3.3 (m, 3H), 3.6 (t, 2H), 3.8 (m, 1H), 4.1 (m, 1H), 4.2 (dd, 1H), 4.3 (s, 2H), 4.5-4.7 (m, 4H), 4.7-4.8 (m, 2H); LCMS: m/z 212 (M+1)$^+$.

Method 9

1-Azetidin-3-yl-4-(tetrahydrofuran-2-ylcarbonyl)piperazine

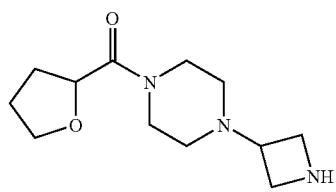

(a) 1-[1-(Diphenylmethyl)azetidin-3-yl]-4-(tetrahydrofuran-2-ylcarbonyl)piperazine The title compound was prepared by utilizing the reductive alkylation protocol described in Method 4a but using 1-(tetrahydrofuran-2-ylcarbonyl)piperazine as the amine (yield, 82%). $^1$H NMR (500 MHz, CD$_3$OD): 1.9-2.0 (m, 3H), 2.0-2.1 (m, 1H), 2.2 (m, 1H), 2.3-2.4 (m, 3H), 3.0 (m, 3H), 3.4 (t, 2H), 3.5-3.6 (m, 1H), 3.6-3.7 (m, 1H), 3.8 (qt, 1H), 3.9 (qt, 1H), 4.5 (s, 1H), 4.7 (t, 1H), 7.2 (t, 2H), 7.3 (t, 4H), 7.4 (t, 4H); LCMS: m/z 406 (M+1)$^+$.

(b) 1-Azetidin-3-yl-4-(tetrahydrofuran-2-ylcarbonyl)piperazine

Palladium hydroxide on carbon (0.15 g) was placed in a 5 mL tube and then a solution of 1-[1-(diphenylmethyl)azetidin-3-yl]-4-(tetrahydrofuran-2-ylcarbonyl)piperazine (0.66 g, 1.6 mmol), methanol (4 mL) and acetic acid (0.3 mL) was added. The mixture was stirred under hydrogen (1.6 bar) at RT for 60 h and then the catalyst was filtered off by means of Celite®. The solvent was removed by evaporation and the crude product was used in the next step without quantification. LCMS: m/z 240 (M+1)+.

Method 10

1-Azetidin-3-yl-4-(methoxyacetyl)piperazine

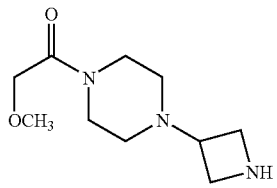

(a) 1-[1-(Diphenylmethyl)azetidin-3-yl]-4-(methoxyacetyl)piperazine

To a solution of 1-[1-(diphenylmethyl)azetidin-3-yl]piperazine (see Method 7a; 615 mg, 2.0 mmol) in DMF (8 mL) were added methoxy acetic acid (272 mg, 3.0 mmol), DIPEA (310 mg, 2.4 mmol) and TBTU (770 mg, 2.4 mmol). The reaction mixture was stirred at RT for 12 h and then partitioned between methylene chloride and aqueous NaHCO₃. The aqueous phase was extracted twice with methylene chloride and then the combined organic solutions were washed with brine and dried over MgSO₄. The solvent was removed by evaporation and the product was purified by means of reversed phase chromatography is using a mixture of acetonitrile and aqueous 0.1 M ammonium acetate as eluent. There was obtained 610 mg (80%) of 1-[1-(diphenylmethyl)azetidin-3-yl]-4-(methoxyacetyl)-piperazine. $^1$H NMR (500 MHz, CD₃OD): 2.3-2.4 (m, 4H), 3.0 (m, 3H), 3.4 (s, 3H), 3.4 m, 2H), 3.5 (m, 2H), 3.6 (m, 2H), 4.1 (s, 2H), 4.5 (s, 1H), 7.2 (t, 2H), 7.3 (t, 4H), 7.4 (d, 41-1); LCMS: m/z 380 (M+1)+.

(b) 1-Azetidin-3-yl-4-(methoxyacetyl)piperazine

The title compound was prepared by utilizing the hydrogenation reaction protocol described in Method 9b but using 1-[1-(diphenylmethyl)azetidin-3-yl]-4-(methoxyacetyl)-piperazine as the substrate. The crude product was used in the next step without quantification. LCMS: m/z 214 (M+1)+.

Method 11

2-(4-Azetidin-3-ylpiperazin-1-yl)-2-oxoethanol

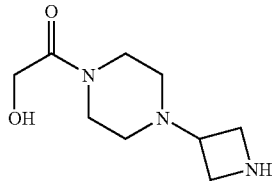

(b) 2-{4-[1-(Diphenylmethyl)azetidin-3-yl]piperazin-1-yl}-2-oxoethanol

The title compound was prepared by utilizing the amide formation reaction protocol described in Method 10a but using 2-hydroxyacetic acid as the carboxylic acid (yield, 54%). $^1$H NMR (500 MHz, CD₃OD): 2.3-2.4 (m, 4H), 3.0 (m, 3H), 3.4 (m, 4H), 3.6 m, 2H), 4.1 (s, 2H), 4.5 (s, 1H), 7.2 (t, 2H), 7.3 (t, 4H), 7.4 (d, 4H); LCMS: m/z 366 (M+1)+.

(b) 2-(4-Azetidin-3-ylpiperazin-1-yl)-2-oxoethanol

The title compound was prepared by utilizing the hydrogenation reaction protocol described in Method 9b but using 2-{4-[1-(diphenylmethyl)azetidin-3-yl]piperazin-1-yl}-2-oxoethanol as the substrate. The crude product was used in the next step without quantification. LCMS: m/z 200 (M+1)+.

Method 12

(9aS)-8-Azetidin-3-ylhexahydropyrazino[2,1-c][1,4]oxazin-4(3H)-one

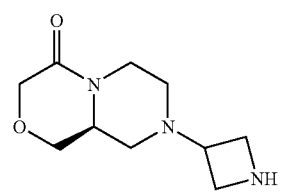

(a) Benzyl (3S)-3-(hydroxymethyl)piperazine-1-carboxylate hydrochloride

4-Benzyl 1-tert-butyl (2S)-2-(hydroxymethyl)piperazine-1,4-dicarboxylate (see WO 02/000631; 1.6 g, 4.6 mmol was dissolved in acetonitrile (25 mL) and to the resultant solution was added concentrated HCl (1 mL). The mixture was stirred at RT overnight and then the solvent was removed by evaporation. There was obtained 1.3 g (100%) of benzyl (3S)-3-(hydroxymethyl)piperazine-1-carboxylate hydrochloride as a colorless oil. $^1$H NMR (500 MHz, CD₃OD): 3.1-3.4 (m, 5H), 3.7 (m, 1H), 3.8 (m, 1H), 4.2 (m, 2H), 5.2 (m, 2H), 7.2-7.4 (m, 5H); LCMS: m/z 251 (M+1)+.

(b) Benzyl (3S)-4-(bromoacetyl)-3-(hydroxymethyl)piperazine-1-carboxylate

Benzyl (3S)-3-(hydroxymethyl)piperazine-1-carboxylate hydrochloride (0.83 g, 2.9 mmol) was dissolved in methylene chloride (10 mL) together with DIPEA (1.5 mL, 8.6 mmol). Bromoacetyl chloride (0.48 g, 3.0 mmol) was added at 0° C. by means of drops. The mixture was stirred at RT for 1 h and then water (10 mL) was added. The phases were separated by means of a phase separator column. The organic solution was collected and the solvent was removed by evaporation. There was obtained 1.1 g (100%) of benzyl (3S)-4-(bromoacetyl)-3-(hydroxymethyl)piperazine-1-carboxylate as a brown oil. LCMS: m/z 370 (M−1)−.

(c) Benzyl (9aS)-4-oxohexahydropyrazino[2,1-c][1,4]oxazine-8(1H)-carboxylate

Benzyl (3S)-4-(bromoacetyl)-3-(hydroxymethyl)piperazine-1-carboxylate (1.1 g, 2.9 mmol was dissolved in toluene (25 mL) and to the resultant solution was added potassium carbonate (4.0 g, 28.8 mmol). The mixture was heated to reflux overnight, cooled to RT and then the solids were filtered off. The solvent was removed by evaporation and the product was purified by chromatography on silica gel (methanol-methylene chloride 1% to 10%). There was obtained 0.19 g (23%) of benzyl (9aS)-4-oxohexahydropyrazino[2,1-c][1,4]oxazine-8(1H)-carboxylate as a colorless oil. $^1$H NMR (500 MHz, CDCl$_3$): 2.6-3.0 (m, 3H), 3.4-3.6 (m, 2H), 4.0 (d, 1H), 4.1-4.3 (m, 4H), 4.5 (d, 1H), 5.1 (s, 2H), 7.2-7.4 (m, 5H).

(d) (9aS)-Hexahydropyrazino[2,1-c][1,4]oxazin-4(3H)-one

Benzyl (9aS)-4-oxohexahydropyrazino[2,1-c][1,4]oxazine-8(1H)-carboxylate (0.19 g, 0.65 mmol was dissolved in ethanol (20 mL). The solution was transferred to a 25 mL vial, which contained 10% palladium on carbon (0.1 g), formic acid (0.1 g, 2.2 mmol) and ammonium formate (0.2 g, 3.17 mmol). The mixture was heated for 5 min at 120° C. using microwave single node heating. The catalyst was filtered off and the solution of crude (9aS)-hexahydropyrazino[2,1-c][1,4]oxazin-4(3H)-one was used in the next step without purification and quantification.

(e) (9aS)-8-[1-(Diphenylmethyl)azetidin-3-yl]hexahydropyrazino[2,1-c][1,4]oxazin-4(3H)-one To a solution of 1-(diphenylmethyl)azetidin-3-one (see Bioorg. Med. Chem. Lett.; 13; 2003; 2191-2194, ~0.65 mmol) and (9aS)-hexahydropyrazino[2,1-c][1,4]oxazin-4(3H)-one (0.65 mmol), in methanol (10 mL) was added a solution of sodium cyano borohydride (125 mg, 2.0 mmol) and zinc chloride (135 mg, 1.0 mmol) in methanol (20 mL). The reaction mixture was stirred at RT for 15 min and then the solvent was removed by evaporation. The residue was partitioned between ethyl acetate (50 mL) and water (20 mL). The organic solution was washed with brine and then dried over Na$_2$SO$_4$. The solvent was removed by evaporation and the residue was dissolved in a mixture of acetonitrile (10 mL), acetic acid (100 mg) and water (10 mL). The product was purified by means of reversed phase chromatography using a mixture of acetonitrile and aqueous 0.1 M ammonium acetate. The proper fractions were combined and concentrated on a rotavapor. The aqueous residue was extracted with ethyl acetate and the organic solution was dried over Na$_2$SO$_4$. The solvent was removed by evaporation and there was obtained 170 mg (69%) of (9aS)-8-[1-(diphenylmethyl)azetidin-3-yl]hexahydropyrazino-[2,1-c][1,4]oxazin-4(3H)-one. $^1$H NMR (400 MHz, CDCl$_3$): 1.6-1.7 (m, 1H), 1.8-1.9 (m, 1H), 2.6 (d, 1H), 2.7-2.8 (m, 21-1), 2.8-2.9 (m, 2H), 3.0 (qn, 1H), 3.3-3.7 (m, 4H), 3.9 (dd, 1H), 4.0-4.2 (qt, 2H), 4.4 (s, 1H), 4.5 (dd, 1H), 7.2 (t, 2H), 7.3 (m, 4H), 7.4 (m, 4H); LCMS: m/z 378 (M+1)$^+$.

(f) (9aS)-8-Azetidin-3-ylhexahydropyrazino[2,1-c][1,4]oxazin-4(3H)-one (9aS)-8-[1-(Diphenylmethyl)azetidin-3-yl]hexahydropyrazino-[2,1-c][1,4]oxazin-4(3H)-one (85 mg, 0.22 mmol) was dissolved in ethanol (18 mL). The solution was transferred to a 25 mL vial, which contained ethanol (2 mL), 10% palladium on carbon (0.1 g), formic acid (0.1 g, 2.2 mmol) and ammonium formate (0.2 g, 3.17 mmol). The mixture was heated for 5 min at 120° C. using microwave single node heating. The catalyst was filtered off and the solution of crude (9aS)-8-azetidin-3-ylhexahydropyrazino[2,1-c][1,4]oxazin-4(3H)-one was used in the next step without purification and quantification.

Method 13

(9aR)-8-azetidin-3-ylhexahydropyrazino[1,4]oxazin-4(3H)-one

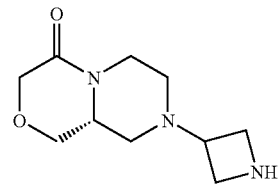

(a) 4-Benzyl 1-tert-butyl (2R)-2-(hydroxymethyl)piperazine-1,4-dicarboxylate (2R)-4-[(Benzyloxy)carbonyl]-1-(tert-butoxycarbonyl)piperazine-2-carboxylic acid (1.4 g, 3.9 mmol) was dissolved in dimethoxyethane (10 mL) and to the cooled resultant solution was added N-methylmorpholine (0.4 g, 3.9 mmol) followed by isobutyl chloroformate (0.54 g, 3.9 mmol) by means of drops. The mixture was stirred at 0° C. for 20 min and then the mixture was filtered. The filtrate was transferred to a 500 mL flask and then cooled again. Sodium borohydride (0.22 g, 5.9 mmol) dissolved in water (5 mL) was added and the external cooling bath was removed. The reaction mixture was stirred until the temperature of it had reached RT whereupon water (120 mL) was added. The mixture was extracted trice with ethyl acetate and the combined organic solutions were dried and then evaporated. The product was purified by column chromatography on silica gel (ethyl acetate-heptane 10% to 70%). There was obtained 1.2 g (84%) of 4-benzyl 1-tert-butyl (2R)-2-(hydroxymethyl)piperazine-1,4-dicarboxylate as a colorless oil. $^1$H NMR (500 MHz, CDCl$_3$): 1.4 (s, 9H), 2.7-3.2 (b, 4H), 3.5 (b, 2H), 3.8-4.2 (m, 4H), 5.1 (m, 2H), 7.2-7.4 (m, 5H); LCMS: m/z 349 (M−1)$^−$.

(b) Benzyl (3R)-3-(hydroxymethyl)piperazine-1-carboxylate hydrochloride

The title compound was prepared by utilizing the hydrolysis reaction protocol described in Example 12a but using 4-benzyl 1-tert-butyl (2R)-2-(hydroxymethyl)piperazine-1,4-dicarboxylate as the substrate (yield, 100%). $^1$H NMR (500 MHz, CD$_3$OD): 3.1-3.4 (m, 5H), 3.7 (m, 1H), 3.8 (m, 1H), 4.2 (m, 2H), 5.2 (m, 2H), 7.2-7.4 (m, 5H); LCMS: m/z 251 (M+1)$^+$.

(c) Benzyl (3R)-4-(bromoacetyl)-3-(hydroxylmethyl)piperazine-1-carboxylate

The title compound was prepared by utilizing the acylation reaction protocol described in Example 12b but using benzyl (3R)-3-(hydroxymethyl)piperazine-1-carboxylate hydrochloride as the amine (yield, 100%). LCMS: m/z 370 (M−1)$^−$.

(d) Benzyl (9aR)-4-oxohexahydropyrazino[2,1-c][1,4]oxazine-8(1H)-carboxylate The title compound was prepared by utilizing the cyclisation reaction protocol described in Example 12c but using benzyl (3R)-4-(bromoacetyl)-3-(hydroxymethyl)piperazine-1-carboxylate as the substrate (yield, 17%). $^1$H NMR (500 MHz, CDCl$_3$): 2.6-3.0 (m, 3H), 3.4-3.6 (m, 2H), 4.0-4.3 (m, 5H), 4.6 (d, 1H), 5.1-5.2 (s, 2H), 7.2-7.4 (m, 5H); LCMS: m/z 291 (M+1)$^+$.

(e) (9aR)-Hexahydropyrazino[2,1-c][1,4]oxazin-4(3H)-one

The title compound was prepared by utilizing the reductive deprotection reaction protocol described in Example 12d but using benzyl (9aR)-4-oxohexahydropyrazino[2,1-c][1,4]oxazine-8(1H)-carboxylate as the substrate. The solution of crude (9aR)-hexahydropyrazino[2,1-c][1,4]oxazin-4(3H)-one was used in the next step without purification and quantification.

(f) (9aR)-8-[1-(Diphenylmethyl)azetidin-3-yl]hexahydropyrazino[2,1-c][1,4]oxazin-4(3H)-one The title compound was prepared by utilizing the reductive allylation reaction protocol described in Example 12e but using (9aR)-hexahydropyrazino[2,1-c][1,4]oxazin-4(3H)-one as the amine (yield, 71%). $^1$H NMR (400 MHz, CDCl$_3$): 1.6-1.7 (t, 1H), 1.8 (dt, 1H), 2.5-2.6 (d, 1H), 2.7-2.8 (m, 2H), 2.8-2.9 (m, 2H), 2.9-3.0 (qn, 1H), 3.3-3.4 (m, 2H), 3.5 (m, 1H), 3.8-3.9 (dd, 1H), 4.0-4.2 (qt, 2H), 4.2-4.3 (s, 1H), 4.4-4.5 (m, 1H), 7.1 (m, 2H), 7.2 (m, 4H), 7.4 (m, 4H); LCMS: m/z 378 (M+1)$^+$.

(g) (9aR)-8-Azetidin-3-ylhexahydropyrazino[2,1-c][1,4]oxazin-4(3H)-one

The title compound was prepared by utilizing the reductive deprotection reaction protocol described in Example 12f but using (9aR)-8-[1-(diphenylmethyl)azetidin-3-yl]hexahydropyrazino-[2,1-c][1,4]oxazin-4(3H)-one as the substrate. The solution of crude (9aR)-8-azetidin-3-ylhexahydropyrazino[2,1-c][1,4]oxazin-4(3H)-one was used in the next step without purification and quantification. LCMS: m/z 212 (M+1)$^+$.

Method 14

1-Azetidin-3-yl-4-(cyclopropylcarbonyl)piperazine

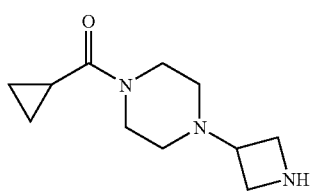

(a) 1-(Cyclopropylcarbonyl)-4-[1-(diphenylmethyl)azetidin-3-yl]piperazine

The title compound was prepared by utilizing the acylation reaction protocol described in Example 7b but using cyclopropanecarbonyl chloride as the acylating agent (yield, 60%). $^1$H NMR (400 MHz, CDCl$_3$): 0.7 (m, 2H), 0.9 (m, 2H), 1.6-1.7 (m, 1H) 2.2-2.4 (b, 4H), 2.8-3.0 (m, 3H), 3.4 (t, 2H), 3.6 (b, 4H), 4.4 (s, 1H), 7.2 (t, 2H), 7.2-7.3 (m, 4H), 7.4 (d, 4H); LCMS: m/z 376 (M+1)$^+$.

(b) 1-Azetidin-3-yl-4-(cyclopropylcarbonyl)piperazine

The title compound was prepared by utilizing the reductive deprotection reaction protocol described in Method 12f but using 1-(cyclopropylcarbonyl)-4-[1-(diphenylmethyl)azetidin-3-yl]piperazine as the substrate. The solution of crude 1-azetidin-3-yl-4-(cyclopropylcarbonyl)piperazine was used in the next step without purification and quantification. LCMS: m/z 210 (M+1)$^+$.

Method 15

1-Azetidin-3-yl-4-butyrylpiperazine

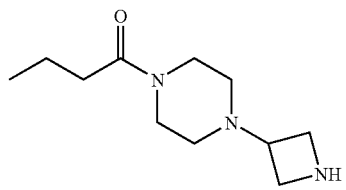

(a) 1-Butyryl-4-[1-(diphenylmethyl)azetidin-3-yl]piperazine

The title compound was prepared by utilizing the acylation reaction protocol described in Example 7b but using butyryl chloride as the acylating agent (yield, 50%). $^1$H NMR (400 MHz, CDCl$_3$): 0.9 (t, 3H), 1.5-1.7 (m, 4H), 2.2-2.3 (m, 4H), 2.8-3.0 (m, 3H), 3.3 (b, 2H), 3.5 (b, 2H), 3.6 (b, 2H), 4.4 (s, 1H), 7.1-7.2 (t, 2H), 7.3 (m, 4H), 7.4 (d, 4H); LCMS: m/z 378 (M+1)$^+$.

(b) 1-Azetidin-3-yl-4-butyrylpiperazine

The title compound was prepared by utilizing the reductive deprotection reaction protocol described in Method 12f but using 1-butyryl-4-[1-(diphenylmethyl)azetidin-3-yl]piperazine as the substrate. The solution of crude 1-azetidin-3-yl-4-butyrylpiperazine was used in the next step without purification and quantification. LCMS: m/z 212 (M+1)$^+$.

Method 16

1-Azetidin-3-yl-4-isobutyrylpiperazine

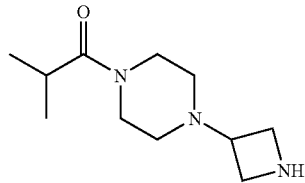

(a) 1-[1-(Diphenylmethyl)azetidin-3-yl]-4-isobutyrylpiperazine

The title compound was prepared by utilizing the acylation reaction protocol described in Example 7b but using isobutyryl chloride as the acylating agent (yield, 59%). $^1$H NMR (400 MHz, CDCl$_3$): 1.1 (d, 6H), 2.3 (m, 4I-1), 2.8 (qn, 1H), 2.9 (t, 2H), 3.0 (qn, 1H), 3.4 (t, 2H), 3.5 (b, 2H), 3.6 (b, 2H), 4.4 (s, 1H), 7.2 (t, 2H), 7.3 (m, 4H), 7.4 (d, 4H); LCMS: m/z 378 (M+1)$^+$.

(b) 1-Azetidin-3-yl-4-isobutyrylpiperazine

The title compound was prepared by utilizing the reductive deprotection reaction protocol described in Method 12f but using 1-[1-(diphenylmethyl)azetidin-3-yl]-4-isobutyrylpiperazine as the substrate. The solution of crude 1-azetidin-3-yl-4-isobutyrylpiperazine was used in the next step without purification and quantification. LCMS: m/z 212 (M+1)$^+$.

The invention claimed is:

1. A compound of formula (I)

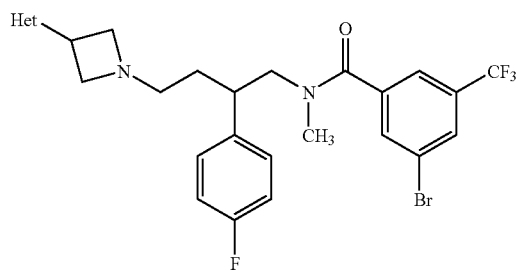

wherein
Het is

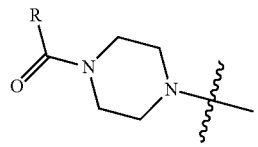

wherein
R is $C_1$-$C_4$ alkyl; cyclopropyl; $C_1$-$C_4$ methoxyalkyl; $C_1$-$C_4$ ethoxyalkyl; $C_1$-$C_4$ hydroxy alkyl; tetrahydrofuran-2-yl; tetrahydrofuran-3-yl; tetrahydropyran-2-yl; tetrahydropyran-3-yl; or tetrahydropyran-4-yl;
or Het is

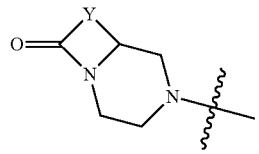

wherein
Y is $C_1$-$C_3$ alkyl; —CH$_2$—O—CH$_2$—; or —CH$_2$—CH$_2$—O—; as well as pharmaceutically and pharmacologically acceptable salts thereof, and enantiomers of the compound of formula (I).

2. A compound according to claim 1 wherein the compound is the (S)-enantiomer.

3. A compound according to claim 1 wherein Het is

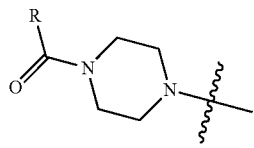

wherein
R is $C_1$-$C_4$ alkyl; $C_1$-$C_4$ methoxyalkyl; $C_1$-$C_4$ ethoxyalkyl; $C_1$-$C_4$ hydroxyalkyl; tetrahydrofuran-2-yl; tetrahydrofuran-3-yl; tetrahydropyran-2-yl; tetrahydropyran-3-yl; or tetrahydropyran-4-yl.

4. A compound according to claim 3, wherein R is $C_1$-$C_2$ methoxyalkyl.

5. A compound according to claim 3, wherein R is $C_1$-$C_2$ ethoxyalkyl.

6. A compound according to claim 3, wherein R is $C_1$-$C_3$ alkyl.

7. A compound according to claim 6, wherein R is $C_1$-$C_2$ alkyl.

8. A compound according to claim 1 wherein Het is

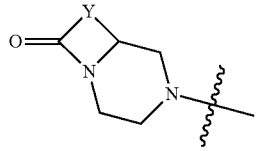

wherein
Y is $C_1$-$C_3$ alkyl; —CH$_2$—O—CH$_2$—; or —CH$_2$—CH$_2$—O—.

9. A compound according to claim 8, wherein Y is $C_1$-$C_3$ alkyl.

10. A compound according to claim 8, wherein Y is —CH$_2$—O—CH$_2$—.

11. A compound according to claim 1 selected from
3-Bromo-N-((2S)-2-(4-fluorophenyl)-4-{3-[(8aR)-6-oxo-hexahydropyrrolo[1,2-a]pyrazin-2(1H)-yl]azetidin-1-yl}butyl)-N-methyl-5-(trifluoromethyl)benzamide;
3-Bromo-N-((2S)-2-(4-fluorophenyl)-4-{3-[(8aS)-6-oxo-hexahydropyrrolo[1,2-a]pyrazin-2(1H)-yl]azetidin-1-yl}butyl)-N-methyl-5-(trifluoromethyl)benzamide;
3-Bromo-N-{(2S)-2-(4-fluorophenyl)-4-[3-(6-oxooctahydro-2H-pyrido[1,2-a]pyrazin-2-yl)azetidin-1-yl]butyl}-N-methyl-5-(trifluoromethyl)benzamide;
3-Bromo-N-((2S)-2-(4-fluorophenyl)-4-{3-[(9aR)-6-oxooctahydro-2H-pyrido[1,2-a]pyrazin-2-yl]azetidin-1-yl}butyl)-N-methyl-5-(trifluoromethyl)benzamide;
3-Bromo-N-((2S)-2-(4-fluorophenyl)-4-{3-[(9aS)-6-oxooctahydro-2H-pyrido[1,2-a]pyrazin-2-yl]azetidin-1-yl}butyl)-N-methyl-5-(trifluoromethyl)benzamide;
3-Bromo-N-{(2S)-2-(4-fluorophenyl)-4-[3-(4-acetylpiperazin-1-yl)azetidin-1-yl]butyl}-N-methyl-5-(trifluoromethy)benzamide;
3-Bromo-N-{(2S)-2-(4-fluorophenyl)-4-[3-(4-propionylpiperazin-1-yl)azetidin-1-yl]butyl}-N-methyl-5-(trifluoromethyl)benzamide;
3-Bromo-N-{(2S)-2-(4-fluorophenyl)-4-[3-(4-oxohexahydropyrazino[2,1-c][1,4]oxazin-8(1H)-yl)azetidin-1-yl]butyl}-N-methyl-5-(trifluoromethy)benzamide;

3-Bromo-N-((2S)-2-(4-fluorophenyl)-4-{3-[4-(tetrahydrofuran-2-ylcarbonyl)piperazin-1-yl]azetidin-1-yl}butyl)-N-methyl-5-(trifluoromethyl)benzamide;

3-Bromo-N-((2S)-2-(4-fluorophenyl)-4-{3-[4(methoxyacetyl)piperazin-1-yl]azetidin-1-yl}butyl)-N-methyl-5-(trifluoromethyl)benzamide;

3-Bromo-N-{(2S)-2-(4-fluorophenyl)-4-[3-(4-glycoloylpiperazin-1-yl)azetidin-1-yl]butyl}-N-methyl-5-(trifluoromethyl)benzamide;

3-Bromo-N-((2S)-2-(4-fluorophenyl)-4-{3-[(9aS)-4-oxohexahydropyrazino[2,1-c][1,4]oxazin-8(1H)-yl]azetidin-1-yl}butyl)-N-methyl-5-(trifluoromethyl)benzamide;

3-Bromo-N-((2S)-2-(4-fluorophenyl)-4-{3-[(9aR)-4-oxohexahydropyrazino[2,1-c][1,4]oxazin-8(1H)-yl]azetidin-1-yl}butyl)-N-methyl-5-(trifluoromethyl)benzamide;

3-Bromo-N-[(2S)-4-{3-[4-(cyclopropylcarbonyl)piperazin-1-yl]azetidin-1-yl}-2-(4-fluorophenyl)butyl]-N-methyl-5-(trifluoromethyl)benzamide;

3-Bromo-N-[(2S)-4-[3-(4-butyrylpiperazin-1-yl)azetidin-1-yl]-2-(4-fluorophenyl)butyl]-N-methyl-5-(trifluoromethyl)benzamide; and 3-Bromo-N-{(2S)-2-(4-fluorophenyl)-4-[3-(4-isobutyrylpiperazin-1-yl)azetidin-1-yl]butyl}-N-methyl-5-(trifluoromethyl)benzamide, or a pharmaceutically acceptable salt thereof.

12. A pharmaceutical formulation comprising a compound according to claim 1 as active an ingredient and a pharmaceutically acceptable carrier or diluent.

13. A compound: 3-Bromo-N-{(2S)-2-(4-fluorophenyl)-4-[3-(4-acetylpiperazin-1-yl)azetidin-1-yl]butyl}-N-methyl-5-(trifluoromethyl)benzamide, or a pharmaceutically acceptable salt thereof.

14. A pharmaceutical formulation comprising a compound according to claim 13 as active an ingredient and a pharmaceutically acceptable carrier or diluent.

15. A compound: 3-Bromo-N-{(2S)-2-(4-fluorophenyl)-4-[3-(4-propionylpiperazin-1-yl)azetidin-1-yl]butyl}-N-methyl-5-(trifluoromethyl)benzamide, or a pharmaceutically acceptable salt thereof.

16. A pharmaceutical formulation comprising a compound according to claim 15 as active an ingredient and a pharmaceutically acceptable carrier or diluent.

17. A compound: 3-Bromo-N-{(2S)-2-(4-fluorophenyl)-4-[3-(4-oxohexahydropyrazino [2,1-c][1,4]oxazin-8(1H)-yl)azetidin-1-yl]butyl}-N-methyl-5-(trifluoromethy)benzamide, or a pharmaceutically acceptable salt thereof.

18. A pharmaceutical formulation comprising a compound according to claim 17 as active an ingredient and a pharmaceutically acceptable carrier or diluent.

19. A compound: 3-Bromo-N-((2S)-2-(4-fluorophenyl)-4-{3-[4(tetrahydrofuran-2-ylcarbonyl)piperazin-1-yl]azetidin-1-yl}butyl)-N-methyl-5-(trifluoromethyl)benzamide, or a pharmaceutically acceptable salt thereof.

20. A pharmaceutical formulation comprising a compound according to claim 19 as active an ingredient and a pharmaceutically acceptable carrier or diluent.

* * * * *

UNITED STATES PATENT AND TRADEMARK OFFICE
CERTIFICATE OF CORRECTION

PATENT NO. : 8,288,370 B2
APPLICATION NO. : 11/992701
DATED : October 16, 2012
INVENTOR(S) : Rolf Bergman It is certified that error appears in the above-identified patent and that said Letters Patent is hereby corrected as shown below:

Title page, Item (56), Line 5 (Other Publications), please delete "Contrained" and insert --Constrained--, therefor.

Column 36, Line 37 (Claim 9), please delete "$C_1$-$C_3$" and insert --$C_2$-$C_3$--, therefor.

Column 36, Line 49 (Claim 11), please delete "[3(6" and insert --[3-(6--, therefor.

Column 36, Lines 59-60 (Claim 11), please delete "(trifluoromethy)" and insert --(trifluoromethyl)--, therefor.

Column 36, Line 63 (Claim 11), please delete "(trifluoromethy)" and insert --(trifluoromethyl)--, therefor.

Column 36, Line 66 (Claim 11), please delete "trifluoromethy)" and insert --(trifluoromethyl)--, therefor.

Column 37, Line 4 (Claim 11), please delete "[4(methoxy" and insert --[4-(methoxy--, therefor.

Column 37, Lines 22-23 (Claim 11), please delete "(trifluoromethy)" and insert --(trifluoromethyl)--, therefor.

Column 37, Line 29 (Claim 12), please delete "active an" and insert --an active--, therefor.

Column 38, Line 6 (Claim 14), please delete "active an" and insert --an active--, therefor.

Column 38, Line 13 (Claim 16), please delete "active an" and insert --an active--, therefor.

Column 38, Line 17 (Claim 17), please delete "(trifluoromethy)" and insert --(trifluoromethyl)--, therefor.

Signed and Sealed this
Nineteenth Day of March, 2013

Teresa Stanek Rea
*Acting Director of the United States Patent and Trademark Office*

CERTIFICATE OF CORRECTION (continued)
U.S. Pat. No. 8,288,370 B2

Column 38, Line 20 (Claim 18), please delete "active an" and insert --an active--, therefor.

Column 38, Line 23 (Claim 19), please delete "[4(tetrahydrofuran" and insert --[4-(tetrahydrofuran--, therefor.

Column 38, Line 27 (Claim 20), please delete "active an" and insert --an active--, therefor.

UNITED STATES PATENT AND TRADEMARK OFFICE
CERTIFICATE OF CORRECTION

| | | |
|---|---|---|
| PATENT NO. | : 8,288,370 B2 | Page 1 of 1 |
| APPLICATION NO. | : 11/992701 | |
| DATED | : October 16, 2012 | |
| INVENTOR(S) | : Bergman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 343 days.

Signed and Sealed this
Seventeenth Day of June, 2014

Michelle K. Lee
*Deputy Director of the United States Patent and Trademark Office*